(12) United States Patent
Guedat et al.

(10) Patent No.: US 7,875,613 B2
(45) Date of Patent: Jan. 25, 2011

(54) TETRACYCLIC INHIBITORS OF CYSTEINE PROTEASES, THE PHARMACEUTICAL COMPOSITIONS THEREOF AND THEIR THERAPEUTIC APPLICATIONS

(75) Inventors: Philippe Guedat, Montenois (FR); Xavier Jacq, Etuz (FR); Frédéric Colland, Puiseux En France (FR); Laurent Daviet, Antony (FR); Etienne Formstecher, Paris (FR); Jean-Christophe Rain, Ermont (FR); Matteo Colombo, Camnago (IT)

(73) Assignee: Hybrigenics SA, Paris (FR)

( * ) Notice: Subject to any disclaimer, the term of this patent is extended or adjusted under 35 U.S.C. 154(b) by 984 days.

(21) Appl. No.: 11/554,056

(22) Filed: Oct. 30, 2006

(65) Prior Publication Data

US 2008/0103149 A1    May 1, 2008

(51) Int. Cl.
*A61K 31/53* (2006.01)
*C07D 487/04* (2006.01)
*C12N 9/99* (2006.01)

(52) U.S. Cl. .................. 514/243; 544/184; 435/184
(58) Field of Classification Search ............... 514/243; 544/184; 435/184
See application file for complete search history.

(56) References Cited

U.S. PATENT DOCUMENTS 6,514,972 B2    2/2003 Zhang et al.
7,196,083 B2 *  3/2007 Zhang et al. ............. 514/243

FOREIGN PATENT DOCUMENTS

WO    WO-01/79209    10/2001

* cited by examiner

*Primary Examiner*—Charanjit S Aulakh
(74) *Attorney, Agent, or Firm*—B. Aaron Schulman; Terry L. Wright; Stites & Harbison PLLC

(57) ABSTRACT

The present invention concerns new compounds of formula (I), their process of preparation and their therapeutic use

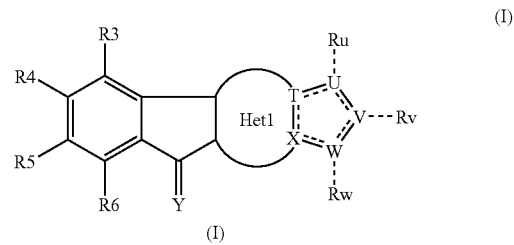

(I)

wherein R3, R4, R5, R6, Y, Het1, T, U, V, W, X, Ru, Rv and Rw are as defined in claim 1.

10 Claims, No Drawings

TETRACYCLIC INHIBITORS OF CYSTEINE PROTEASES, THE PHARMACEUTICAL COMPOSITIONS THEREOF AND THEIR THERAPEUTIC APPLICATIONS

The present invention concerns new inhibitors of cysteine proteases, their process of preparation and their therapeutic use.

Proteases can be categorized based on their substrate specificities or mechanisms of catalysis. Upon the basis of the mechanism of peptide hydrolysis, five major protease classes are known: serine, cysteine, aspartic, threonine and metallo-proteases. Cysteine proteases comprise, inter allia, de-ubiquitination enzymes, caspases, cathepsins, calpains as well as viral, bacterial or parasitic cysteine proteases.

De-ubiquitination enzymes include Ubiquitin Specific Proteases (USPs) and Ubiquitin Carboxy Hydrolases (UCHs). Broadly speaking, the ubiquitin pathway regulates protein degradation and is more particularly involved in cancer, in neurodegenerative diseases such as Alzheimer's disease, Parkinson's disease, in inflammation, in viral infectivity and latency (in particular for Herpes simplex virus-1, Epstein-Barr virus, SARS coronavirus), or in cardiovascular diseases (*Chem. Rev.* 1997, 97, p. 133-171; *Chem. Rev.* 2002, 102, p. 4459-4488; *J. Biochem.* 2003, 134, p. 9-18; *J. Virology*, 2005, 79(7), p. 4550-4551; *Cardiovasc. Res.* 2004, 61, p. 11-21).

Caspases have been shown to be involved in apoptosis and hence are targets in hepatitis, liver failure, inflammation, cardiac ischemia and failure, renal failure, neurodegeneration, deafness, diabetes, or stroke (*J. Pharmacol Exp. Ther.*, 2004, 308(3), p. 1191-1196, *J. Cell. Physiol.*, 2004, 200(2), p. 177-200; *Kidney Int*, 2004, 66(2), p. 500-506; *Am. J. Pathol.*, 2004, 165(2), p. 353-355; *Mini Rev. Chem.*, 2004, 4(2), p. 153-165; *Otol. Neurotol.*, 2004, 25(4), p. 627-632; Ref. 7, 21, 22, 23, 24, 25).

Cathepsins generally have been shown to be involved in cancer and metastasis, inflammation, immunology/immunoregulation (*Eur. Respir. J.*, 2004, 23(4), p. 620-628) and atherosclerosis (*Ageing Res. Rev.* 2003, 2(4), p. 407-418). More particularly, cathepsins include cathepsin B and B-like which are implicated in cancer and metastasis, and arthritis (*Cancer Metastasis Rev.*, 2003, 22(2-3), p. 271-286; *Biol. Chem.*, 2003, 384(6), p. 845-854 and *Biochem. Soc. Symp.*, 2003, 70, p. 263-276), cathepsin D, involved in particular in cancer and metastasis (*Clin. Exp. Metastasis*, 2004, 21(2), p. 91-106), cathepsin K acting in osteoporosis and arthritis (*Int. J. Pharm.*, 2004, 277(1-2), p. 73-79), cathepsin S which has been shown to play a role in antigen presentation in immunology (*Drug News Perspective*, 2004, 17(6), p. 357-363).

Calpains play a role in ageing in general (*Ageing Res. Rev.* 2003, 2(4), p. 407-418), as well as diabetes (*Mol. Cell. Biochem.*, 2004, 261(1), p. 161-167) and cataract (*Trends Mol. Med.*, 2004, 10(2), p. 78-84) more particularly.

Viral cysteine proteases have been identified in rhinoviruses, poliomyelitis virus, hepatitis A virus, hepatitis C virus, adenovirus, or SARS coronavirus (*Chem. Rev.* 1997, 97, p. 133-171; *Chem. Rev.* 2002, 102, p. 4459-4488; *J. Virology*, 2005, 79(7), p. 4550-4551 and *Acta Microbiol. Immunol. Hung.*, 2003, 50(1), p. 95-101).

Bacterial cysteine proteases include streptopain, staphylococcal cysteine protease, clostripain or gingipains; yeasts such as *Aspergillus flavus* have also been shown to express cysteine proteases which may constitute a virulence factor (*Chem. Rev.* 1997, 97, p. 133-171).

Parasitic cysteine proteases have been reviewed in *Molecular & Biochemical Parasitology* (2002, 120, p. 1-21) and *Chem. Rev.* (2002, 102, p. 4459-4488) for example. It is worth noting that the parasitic agents responsible for most major parasitic diseases are making use of their own cysteine proteases at some point or another of their infective, nutritive or reproductive cycles; such diseases include malaria, Chagas' disease, African trypanosomiasis, leishmaniasis, giardiasis, trichomoniasis, amoebiasis, crypto-sporidiasis, toxoplamiasis, schistosomiasis, fasciolasis, onchocercosis, and other infections by some other flat or round worms.

Therefore, identifying a novel class of inhibitors of cysteine proteases is of significant importance in a wide range of diseases and pathological conditions.

U.S. Pat. No. 6,514,927, WO01/79209 and WO02/02562 disclose compounds comprising 4 fused cycles. However, their use as cysteine protease inhibitors is not suggested.

According to a first object, the present invention concerns a compound of formula (I):

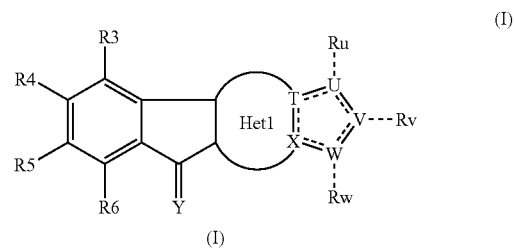

wherein:

⁓⁓⁓ is either a single or double bond, as appropriate;
----- is either none or a single bond, as appropriate;

is a 5 to 7-membered heterocycle, preferably heteroaryl comprising 1 to 5 heteroatoms optionally substituted by one or more substituents chosen from the group consisting in H, CN, =O, Hal, Alk, OAlk, OH, NRCN, C(CN)=C(OH)(OAlk), SR, NRR', C(O)NRR', Heterocycle, Aryl, Heteroaryl, where Alk, Aryl, Heteroaryl, heterocycle are optionally substituted by Hal, NRR', CN, OH, $CF_3$, Aryl, Heteroaryl, OAlk;

where

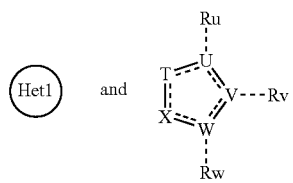

are fused together by T and X;

Y is N—OR1, NR'1, CR2R'2;

R1 is H, Alkyl, Alkenyl, Alkoxyalkyl, Aryloxyalkyl, Aralkyl, Alkoxycarbonylalkyl, Carboxyalkyl;

R'1 is H, Alkyl, Aryl or Aralkyl;

R2, R'2 are each the same or different and are independently selected from H, Alkyl, Aryl or Aralkyl;

T, U, V, W, X are the same or different and may be chosen from C, N, O, S.

Ru, Rv, Rw are the same or different and may be chosen from the group consisting in H, CN, =O, Hal, Alk, OAlk, OH, NRCN, C(CN)=C(OH)(OAlk), SR, NRR', C(O)NRR', Heterocycle, Aryl, Heteroaryl, Cycloalkyl where Alk, Aryl, Heteroaryl, heterocycle, Cycloalkyl are optionally substituted by Hal, NRR', CN, OH, CF$_3$, Aryl, Heteroaryl, OAlk.

R3, R4, R5, R6 are each identical or different and are independently chosen from the group consisting in H, OAlk, Alk, Hal, NRR', CN, OH, OCF$_3$, CF$_3$, Aryl, Heteroaryl;

R and R' are each identical or different and are independently chosen from the group consisting in H, Alk, wherein Alk is optionally substituted by Hal, NRR', CN, OH, CF$_3$, Aryl, Heteroaryl;

or their pharmaceutically acceptable salts, hydrates, or hydrated salts, or the polymorphic crystalline structures of these compounds or their optical isomers, racemates, diastereomers or enantiomers, or their regioisomers, geometrical isomers (E and Z) or mixtures thereof.

Preferably, T, U, V, W, X are C or N.

Preferably, Y is N—OR1 or NR'1, more preferably N—OR1, notably N—OH, N-Alkyl, N—OAlkenyl, N—OAlkyl-O-Alkyl, N—O-Alkyl-CO—OAlkyl, N—O-Alkyl-COOH.

It will be appreciated that when Y is CR2R2', R2 and/or R2' cannot form a fused ring with the rest of the structure of formula (I).

Preferably,

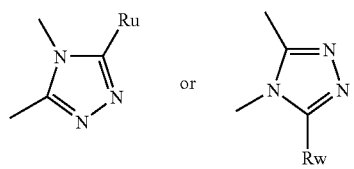

contains 2 or 3 heteroatoms; more preferably, 2 or 3 N.

Most preferably,

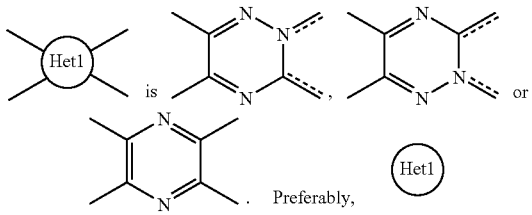

is unsubstituted.

Preferably, Ru, Rv, Rw is chosen from H, Aryl, Alk, NRR', Hal, -AlkAryl, -AlkOH, -AlkOAlk, Cycloalkyl.

Preferably,

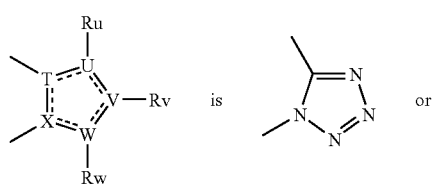

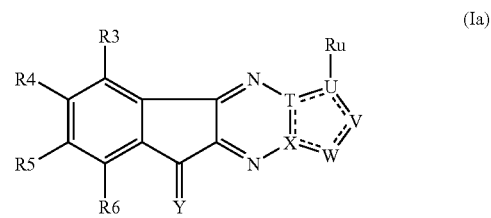

where Rw is H.

Preferably, R3, R4, R5, R6 are each identical or different and are independently chosen from the group consisting in H, Hal, Alk, OAlk, OCF$_3$.

Preferably, R and R' are each identical or different and are independently chosen from the group consisting in H, Alk.

Preferably, Rv, Rw are either H or absent.

Preferred compounds of formula (I) are those of formula (Ia):

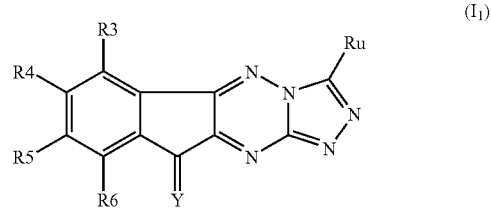

(Ia)

Most preferred compounds are notably those of formulae (I$_1$) to (I$_4$)

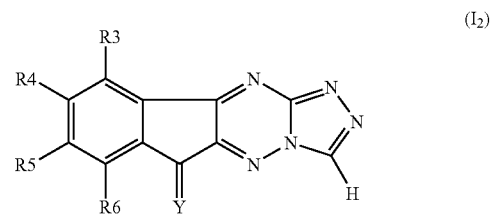

(I$_1$)

(I$_2$)

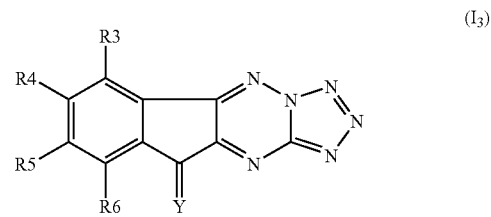

(I$_3$)

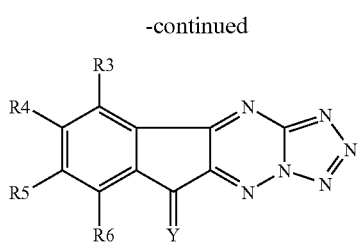

(I4)

Preferred compounds of the invention are chosen from the group consisting in:
- 3-Methyl-1,2,3a,4,10-pentaaza-cyclopenta[b]fluoren-9-one O-methyl-oxime
- 3-Methyl-1,2,3a,4,10-pentaaza-cyclopenta[b]fluoren-9-one O-allyl-oxime
- 1-Methyl-2,3,4,10,10a-pentaaza-cyclopenta[b]fluoren-9-one O-allyl-oxime
- 3-Butyl-1,2,3a,4,10-pentaaza-cyclopenta[b]fluoren-9-one O-allyl-oxime
- 1-Butyl-2,3,4,10,10a-pentaaza-cyclopenta[b]fluoren-9-one O-allyl-oxime
- 1,2,3,3a,4,10-hexaaza-cyclopenta[b]fluoren-9-one O-allyl-oxime
- 1,2,3,3a,4,10-hexaaza-cyclopenta[b]fluoren-9-one oxime
- 1,2,3,3a,4,10-Hexaaza-cyclopenta[b]fluoren-9-one O-decyl-oxime
- 1,2,3,3a,4,10-Hexaaza-cyclopenta[b]fluoren-9-one O-(2-methoxy-ethyl)-oxime
- 1,2,3,3a,4,10-Hexaaza-cyclopenta[b]fluoren-9-one O-(3-phenoxy-propyl)-oxime
- 1-Ethyl-2,3,4,10,10a-pentaaza-cyclopenta[b]fluoren-9-one O-methyl-oxime
- 3-Ethyl-1,2,3a,4,10-pentaaza-cyclopenta[b]fluoren-9-one O-methyl-oxime
- 1-Ethyl-2,3,4,10,10a-pentaaza-cyclopenta[b]fluoren-9-one O-ethyl-oxime
- 3-Ethyl-1,2,3a,4,10-pentaaza-cyclopenta[b]fluoren-9-one O-ethyl-oxime
- 1-Ethyl-2,3,4,10,10a-pentaaza-cyclopenta[b]fluoren-9-one O-allyl-oxime
- 3-Ethyl-1,2,3a,4,10-pentaaza-cyclopenta[b]fluoren-9-one O-allyl-oxime
- 1-Ethyl-2,3,4,10,10a-pentaaza-cyclopenta[b]fluoren-9-one O-benzyl-oxime
- 3-Ethyl-1,2,3a,4,10-pentaaza-cyclopenta[b]fluoren-9-one O-benzyl-oxime
- [1-Ethyl-2,3,4,10,10a-pentaaza-cyclopenta[b]fluoren-9-ylidene]-phenyl-amine
- (1,2,3,3a,4,10-Hexaaza-cyclopenta[b]fluoren-9-ylidene-aminooxy)-acetic acid ethyl ester
- (1,2,3,3a,4,10-Hexaaza-cyclopenta[b]fluoren-9-ylidene-aminooxy)-acetate lithium salt, or their pharmaceutically acceptable salts, hydrates, or hydrated salts, or the polymorphic crystalline structures of these compounds or their optical isomers, racemates, diastereomers or enantiomers, or their regioisomers, geometrical isomers (E and Z) or mixtures thereof.

Most preferred compounds are notably selected from the group consisting in:
- 3-Methyl-1,2,3a,4,10-pentaaza-cyclopenta[b]fluoren-9-one O-methyl-oxime
- 3-Methyl-1,2,3a,4,10-pentaaza-cyclopenta[b]fluoren-9-one O-allyl-oxime
- 3-Butyl-1,2,3a,4,10-pentaaza-cyclopenta[b]fluoren-9-one O-allyl-oxime
- 1,2,3,3a,4,10-hexaaza-cyclopenta[b]fluoren-9-one O-allyl-oxime
- 1,2,3,3a,4,10-hexaaza-cyclopenta[b]fluoren-9-one oxime
- 1,2,3,3a,4,10-Hexaaza-cyclopenta[b]fluoren-9-one O-decyl-oxime
- 1,2,3,3a,4,10-Hexaaza-cyclopenta[b]fluoren-9-one O-(2-methoxy-ethyl)-oxime
- 1,2,3,3a,4,10-Hexaaza-cyclopenta[b]fluoren-9-one O-(3-phenoxy-propyl)-oxime
- 3-Ethyl-1,2,3a,4,10-pentaaza-cyclopenta[b]fluoren-9-one O-methyl-oxime
- 3-Ethyl-1,2,3a,4,10-pentaaza-cyclopenta[b]fluoren-9-one O-ethyl-oxime
- 3-Ethyl-1,2,3a,4,10-pentaaza-cyclopenta[b]fluoren-9-one O-allyl-oxime
- (1,2,3,3a,4,10-Hexaaza-cyclopenta[b]fluoren-9-ylidene-aminooxy)-acetic acid ethyl ester
- (1,2,3,3a,4,10-Hexaaza-cyclopenta[b]fluoren-9-ylidene-aminooxy)-acetate lithium salt, or their pharmaceutically acceptable salts, hydrates, or hydrated salts, or the polymorphic crystalline structures of these compounds or their optical isomers, racemates, diastereomers or enantiomers, or their regioisomers, geometrical isomers (E and Z) or mixtures thereof.

As used hereabove or hereafter:

Alk represents alkyl, alken or alkyn.

"Alkyl" means an aliphatic hydrocarbon group which may be straight or branched having 1 to 20 carbon atoms in the chain. Preferred alkyl groups have 1 to 12 carbon atoms in the chain. "Branched" means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl.

"Alken" means an aliphatic hydrocarbon group containing a carbon-carbon double bond and which may be straight or branched having 2 to 15 carbon atoms in the chain. Preferred alkenyl groups have 2 to 12 carbon atoms in the chain; and more preferably about 2 to 4 carbon atoms in the chain. Exemplary alkenyl groups include ethenyl, propenyl, n-butenyl, i-butenyl, 3-methylbut-2-enyl, n-pentenyl, heptenyl, octenyl, nonenyl, decenyl.

"Alkyn" means an aliphatic hydrocarbon group containing a carbon-carbon triple bond and which may be straight or branched having 2 to 15 carbon atoms in the chain. Preferred alkynyl groups have 2 to 12 carbon atoms in the chain; and more preferably 2 to 4 carbon atoms in the chain. Exemplary alkynyl groups include ethynyl, propynyl, n-butynyl, 2-butynyl, 3-methylbutynyl, n-pentynyl, heptynyl, octynyl and decynyl.

"Alkoxyalkyl" means an alkyl-O-alkyl group wherein the alkyl groups are independently as defined herein. An example of alkoxyalkyl is methoxyethyl.

"Alkoxycarbonylalkyl" means an alkyl-O—CO-alkyl-group wherein the alkyl groups are independently as defined herein. Exemplary alkoxy carbonyl alkyl groups include methoxy- and ethoxy-carbonyl methyl and carbonyl ethyl groups.

"Halogen atom" refers to fluorine, chlorine, bromine or iodine atom; preferably fluorine and chlorine atom.

"Aryl" means an aromatic monocyclic or multicyclic hydrocarbon ring system of 6 to 14 carbon atoms, preferably of 6 to 10 carbon atoms. Exemplary aryl groups include phenyl or naphthyl.

"Arylalkyl" means an aryl-alkyl-group wherein the aryl and alkyl groups are as defined herein. An example of arylalkyl groups is benzyl.

"Aryloxyalkyl" mean an aryl-O-alkyl-group wherein the alkyl and aryl groups are as defined herein. An exemplary aryloxyalkyl group is phenoxypropryl.

As used herein, the terms "heterocycle" or "heterocyclic" refer to a saturated, partially unsaturated or unsaturated, non aromatic stable 3 to 14, preferably 5 to 10 membered mono, bi or multicyclic rings wherein at least one member of the ring is a hetero atom. Typically, heteroatoms include, but are not limited to, oxygen, nitrogen, sulfur, selenium, and phosphorus atoms. Preferable heteroatoms are oxygen, nitrogen and sulfur.

Suitable heterocycles are also disclosed in *The Handbook of Chemistry and Physics,* 76$^{th}$ Edition, CRC Press, Inc., 1995-1996, p. 2-25 to 2-26, the disclosure of which is hereby incorporated by reference.

Preferred non aromatic heterocyclic include, but are not limited to pyrrolidinyl, pyrazolidinyl, imidazolidinyl, oxiranyl, tetrahydrofuranyl, dioxolanyl, tetrahydro-pyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydro-pyridyl, dihydropyridyl, tetrahydropyrinidinyl, dihydrothiopyranyl, azepanyl, as well as the fused systems resulting from the condensation with a phenyl group.

As used herein, the term "heteroaryl" or aromatic heterocycles refers to a 5 to 14, preferably 5 to 10 membered aromatic hetero, mono-, bi- or multicyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Carboxyalkyl" means a HOOC-alkyl-group wherein the alkyl group is as defined herein. Preferred groups include carboxymethyl and carboxyethyl.

"Alkyl", "cycloalkyl", "alkenyl", "alkynyl", "aryl", "heteroaryl", "heterocycle" and the likes refers also to the corresponding "alkylene", "cycloalkylene", "alkenylene", "alkynylene", "arylene", "heteroarylene", "heterocyclene" and the likes which are formed by the removal of two hydrogen atoms.

As used herein, the term "patient" refers to either an animal, such as a valuable animal for breeding, company or preservation purposes, or preferably a human or a human child, which is afflicted with, or has the potential to be afflicted with one or more diseases and conditions described herein.

As used herein, a "therapeutically effective amount" refers to an amount of a compound of the present invention which is effective in preventing, reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

As used herein, the term "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences,* 17$^{th}$ ed., Mack Publishing Company, Easton, Pa., 1985, p. 1418, the disclosure of which is hereby incorporated by reference.

The compounds of the general formula (I) having geometrical isomers, regioisomers and stereoisomers are also a part of the invention.

According to a further object, the present invention is also concerned with the process of preparation of the compounds of formula (I).

The compounds and process of the present invention may be prepared in a number of ways well-known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations,* Wiley-VCH Publishers, 1999.

It will be appreciated that the compounds of the present invention may contain one or more asymmetrically substituted carbon atoms, and may be isolated in optically active or racemic forms. Thus, all chiral, diastereomeric, racemic forms, isomeric forms of a structure are intended, unless the specific stereochemistry or isomeric form is specifically indicated. It is well-known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Additionally, the process of the invention may lead to several regioisomers which are all encompassed by the present invention. Regioisomers are generally isolated by chromatography.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, 3$^{rd}$ ed., John Wiley and Sons, 1999; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether and tetrahydrofuran.

The reactions can take place over a wide range of temperatures. In general, it is found convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

The process of preparation of a compound of formula (I) of the invention is a further object of the present invention.

According to a first aspect, compounds of the invention of formula (I) can be obtained from reacting corresponding compounds of formula (II) and (III):

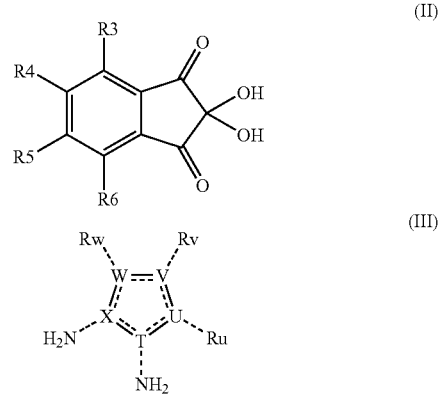

wherein R3, R4, R5, R6, T, U, V, W, X, Ru, Rv, Rw are defined as in formula (I).

Generally, the reaction is carried out in an organic protic solvent, such as an alcohol (preferably ethanol), in the presence of an acid such as acetic acid.

Alternatively and/or cumulatively, compounds of formula (I) may be obtained from corresponding compounds of formula (I'):

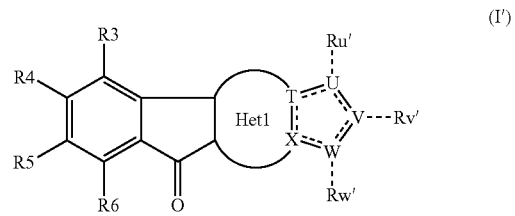

wherein R3, R4, R5, R6, Het1, T, U, V, W, X, Ru, Rv, Rw are defined as in formula (I), wherein each of Ru', Rv', Rw' is similar to Ru, Rv, Rw or is a precursor group of corresponding Ru, Rv, Rw, by one or more step allowing a precursor group to be transformed into the desired Ru, Rv or Rw group.

According to the present invention, the expression "precursor group" of a functional group refers to any group which can, by one or more reactions, lead to the desired function, by means of one or more suitable reagents. Those reactions include de-protection, as well as usual addition, substitution or functionalization reactions.

Compounds of formula (I') may be obtained from corresponding compounds of formula (II) and (III) as discussed above.

Compounds of formula (I) may notably be obtained from compounds of formula (I') disclosed in EP 05292612.8.

The above reactions can be carried out by the skilled person by applying or adapting the methods illustrated in the examples hereinafter.

Further, the process of the invention may also comprise the additional step of isolating the compound of formula (I). This can be done by the skilled person by any of the known conventional means, such as the recovery methods described above.

The starting products (II) and (III) are commercially available or may be obtained by applying or adapting any known methods or those described in the examples.

The synthesis may also be carried out in one pot as a multicomponent reaction.

According to a further object, the present invention concerns also the pharmaceutical compositions comprising a compound of formula (I) as defined below:

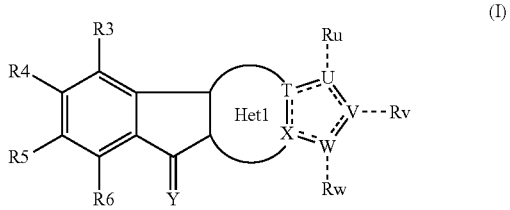

wherein
- ⸺ is either a single or double bond, as appropriate;
- ----- is either none or a single bond, as appropriate;

is a 5 to 7-membered heterocycle, preferably heteroaryl comprising 1 to 5 heteroatoms optionally substituted by one or more substituents chosen from the group consisting in H, CN, =O, Hal, Alk, OAlk, OH, NRCN, C(CN)=C(OH)(OAlk), SR, NRR', C(O)NRR', Heterocycle, Aryl, Heteroaryl, where Alk, Aryl, Heteroaryl, heterocycle are optionally substituted by Hal, NRR', CN, OH, CF$_3$, Aryl, Heteroaryl , OAlk;

where

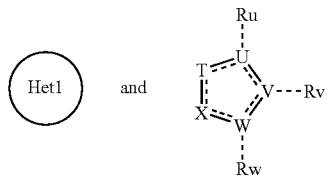

are fused together by T and X;
Y is N—OR1, NR'1, CR2R'2;
R1 is H, Alkyl, Alkenyl, Alkoxyalkyl, Aryloxyalkyl, Arylalkyl, Alkoxycarbonylalkyl, Carboxyalkyl;
R'1 is H, Alkyl, Aryl or Aralkyl;
R2, R'2 are each the same or different and are independently selected from H, Alkyl, Aryl or Aralkyl;
T, U, V, W, X are the same or different and may be chosen from C, N, O, S.
Ru, Rv, Rw are the same or different and may be chosen from the group consisting in H, CN, =O, Hal, Alk, OAlk, OH, NRCN, C(CN)=C(OH)(OAlk), SR, NRR', C(O)NRR', Heterocycle, Aryl, Heteroaryl, heterocycle, Cycloalkyl where Alk, Aryl, Heteroaryl, heterocycle, Cycloalkyl are optionally substituted by Hal, NRR', CN, OH, CF$_3$, Aryl, Heteroaryl, OAlk.
R3, R4, R5, R6 are each identical or different and are independently chosen from the group consisting in H, OAlk, Alk, Hal, NRR', CN, OH, OCF$_3$, CF$_3$, Aryl, Heteroaryl;
R and R' are each identical or different and are independently chosen from the group consisting in H, Alk, wherein Alk is optionally substituted by Hal, NRR', CN, OH, CF$_3$, Aryl, Heteroaryl;

or their pharmaceutically acceptable salts, hydrates, or hydrated salts, or the polymorphic crystalline structures of these compounds or their optical isomers, racemates, diastereomers or enantiomers, or their geometrical isomers (E and Z) or mixtures thereof.

Preferably, T, U, V, W, X are C or N.

Other preferred embodiments of formula (I) are as defined above in respect of the compounds of the invention.

Preferred compounds for the therapeutic use according to the invention are chosen from the group consisting in:

3-Methyl-1,2,3a,4,10-pentaaza-cyclopenta[b]fluoren-9-one O-methyl-oxime

3-Methyl-1,2,3a,4,10-pentaaza-cyclopenta[b]fluoren-9-one O-allyl-oxime

1-Methyl-2,3,4,10,10a-pentaaza-cyclopenta[b]fluoren-9-one O-allyl-oxime

3-Butyl-1,2,3a,4,10-pentaaza-cyclopenta[b]fluoren-9-one O-allyl-oxime

1-Butyl-2,3,4,10,10a-pentaaza-cyclopenta[b]fluoren-9-one O-allyl-oxime 1,2,3,3a,4,10-hexaaza-cyclopenta[b]fluoren-9-one O-allyl-oxime 1,2,3,3a,4,10-hexaaza-cyclopenta[b]fluoren-9-one oxime 1,2,3,3a,4,10-Hexaaza-cyclopenta[b]fluoren-9-one O-decyl-oxime 1,2,3,3a,4,10-Hexaaza-cyclopenta[b]fluoren-9-one O-(2-methoxy-ethyl)-oxime 1,2,3,3a,4,10-Hexaaza-cyclopenta[b]fluoren-9-one O-(3-phenoxy-propyl)-oxime 1-Ethyl-2,3,4,10,10a-pentaaza-cyclopenta[b]fluoren-9-one O-methyl-oxime 3-Ethyl-1,2,3a,4,10-pentaaza-cyclopenta[b]fluoren-9-one O-methyl-oxime 1-Ethyl-2,3,4,10,10a-pentaaza-cyclopenta[b]fluoren-9-one O-ethyl-oxime 3-Ethyl-1,2,3a,4,10-pentaaza-cyclopenta[b]fluoren-9-one O-ethyl-oxime 1-Ethyl-2,3,4,10,10a-pentaaza-cyclopenta[b]fluoren-9-one O-allyl-oxime 3-Ethyl-1,2,3a,4,10-pentaaza-cyclopenta[b]fluoren-9-one O-allyl-oxime 1-Ethyl-2,3,4,10,10a-pentaaza-cyclopenta[b]fluoren-9-one O-benzyl-oxime 3-Ethyl-1,2,3a,4,10-pentaaza-cyclopenta[b]fluoren-9-one O-benzyl-oxime

[1-Ethyl-2,3,4,10,10a-pentaaza-cyclopenta[b]fluoren-9-ylidene]-phenyl-amine (1,2,3,3a,4,10-Hexaaza-cyclopenta[b]fluoren-9-ylidene-aminooxy)-acetic acid ethyl ester (1,2,3,3a,4,10-Hexaaza-cyclopenta[b]fluoren-9-ylidene-aminooxy)-acetate lithium salt, or their pharmaceutically acceptable salts, hydrates, or hydrated salts, or the polymorphic crystalline structures of these compounds or their optical isomers, racemates, diastereomers or enantiomers, or their regioisomers, geometrical isomers (E and Z) or mixtures thereof.

Most preferred compounds for the therapeutic use according to the invention are notably selected from the group consisting in:

3-Methyl-1,2,3a,4,10-pentaaza-cyclopenta[b]fluoren-9-one O-methyl-oxime

3-Methyl-1,2,3a,4,10-pentaaza-cyclopenta[b]fluoren-9-one O-allyl-oxime
3-Butyl-1,2,3a,4,10-pentaaza-cyclopenta[b]fluoren-9-one O-allyl-oxime
1,2,3,3a,4,10-hexaaza-cyclopenta[b]fluoren-9-one O-allyl-oxime
1,2,3,3a,4,10-hexaaza-cyclopenta[b]fluoren-9-one oxime
1,2,3,3a,4,10-Hexaaza-cyclopenta[b]fluoren-9-one O-decyl-oxime
1,2,3,3a,4,10-Hexaaza-cyclopenta[b]fluoren-9-one O-(2-methoxy-ethyl)-oxime
1,2,3,3a,4,10-Hexaaza-cyclopenta[b]fluoren-9-one O-(3-phenoxy-propyl)-oxime
3-Ethyl-1,2,3a,4,10-pentaaza-cyclopenta[b]fluoren-9-one O-methyl-oxime
3-Ethyl-1,2,3a,4,10-pentaaza-cyclopenta[b]fluoren-9-one O-ethyl-oxime
3-Ethyl-1,2,3a,4,10-pentaaza-cyclopenta[b]fluoren-9-one O-allyl-oxime
(1,2,3,3a,4,10-Hexaaza-cyclopenta[b]fluoren-9-ylidene-aminooxy)-acetic acid ethyl ester
(1,2,3,3a,4,10-Hexaaza-cyclopenta[b]fluoren-9-ylidene-aminooxy)-acetate lithium salt, or their pharmaceutically acceptable salts, hydrates, or hydrated salts, or the polymorphic crystalline structures of these compounds or their optical isomers, racemates, diastereomers or enantiomers, or their regioisomers, geometrical isomers (E and Z) or mixtures thereof.

According to a still further object, the present invention concerns the use of a compound of formula (I), as defined above in respect of the pharmaceutical composition, for the preparation of a medicament for inhibiting cysteine protease.

The compounds of the invention are useful for inhibiting cysteine proteases, in particular de-ubiquitination enzymes (such as USPs and UCHs), caspases, cathepsins (in particular cathepsin B, D, K, S and the like), calpains as well as viral, bacterial or parasitic cysteine proteases in patients in the need thereof.

The compounds of the invention are particularly useful for treating and/or preventing cancer and metastasis, more particularly prostate and/or colon cancers, neurodegenerative diseases such as Alzheimer's disease and Parkinson's disease, deafness, disorders associated with ageing, inflammatory disorders, arthritis, osteoporosis, hepatitis, liver failure, cardiac ischemia and failure, stroke, atherosclerosis, renal failure, diabetes, cataract; viral acute or latent infections by Herpes simplex virus-1, Epstein-Barr virus, SARS coronavirus, rhinoviruses, poliomyelitis virus, hepatitis A virus, hepatitis C virus, adenoviruses, and the like; bacterial or fungal infections by pathogenic agents belonging to the *Streptococcus* sp., *Staphylococcus* sp., *Clostidium* sp., *Aspergillus* sp., genera and the like; protozoal infections by species members of the *Trypanosoma* sp., *Plasmodium* sp., *Leishmania* sp., *Trichomonas* sp., *Entamoeba* sp., *Giardia* sp., *Toxoplasma* sp., *Cryptosporidium* sp., genera and the like; flat or round worm infections by species members of the *Fasciola* sp., *Schistosoma* sp., *Onchocerca* sp., *Ascaris* sp., *Taenia* sp., *Caenorhabitis* sp., *Toxocara* sp., *Haemonchus* sp., *Ancylostoma* sp., *Trichuris* sp., *Trichinella* sp., *Strongyloides* sp., *Brugia* sp., genera and the like; as well as immunological, immunoregulatory or antigen presentation disorders.

The present invention also concerns the corresponding methods of treatment comprising the administration of a compound of the invention together with a pharmaceutically acceptable carrier or excipient to a patient in the need thereof.

The identification of those subjects who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I), which is required to achieve the desired biological effect, will vary depending upon a number of factors, including the chemical characteristics (e.g. hydrophobicity) of the compounds employed, the potency of the compounds, the type of disease, the species to which the patient belongs, the diseased state of the patient, the route of administration, the bioavailability of the compound by the chosen route, all factors which dictate the required dose amounts, delivery and regimen to be administered.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well-known in the art. Except insofar as any conventional media or agent is incompatible with the active ingredient, its use in the therapeutic compositions is contemplated. Supplementary active ingredients can also be incorporated into the compositions as suitable therapeutic combinations.

In the context of the invention, the term "treating" or "treatment", as used herein, means reversing, alleviating, inhibiting the progress of, or preventing the disorder or condition to which such term applies, or one or more symptoms of such disorder or condition.

"Therapeutically effective amount" means an amount of a compound/medicament according to the present invention effective in preventing or treating a pathological condition requiring the inhibition of an active cysteine protease involved in its pathogenesis.

According to the invention, the term "patient", or "patient in need thereof", is intended for an animal or a human being affected or likely to be affected with a pathological condition involving an active cysteine protease in its pathogenesis. Preferably, the patient is human.

In general terms, the compounds of this invention may be provided in an aqueous physiological buffer solution containing 0.1 to 10% w/v compound for parenteral administration. Typical dose ranges are from 1 µg/kg to 0.1 g/kg of body weight per day; a preferred dose range is from 0.01 mg/kg to 10 mg/kg of body weight per day or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the compound by the chosen delivery route, and the speed (bolus or continuous infusion) and schedule of administrations (number of repetitions in a given period of time).

The compounds of the present invention are also capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical total daily dose ranges are from 0.01 to 100 mg/kg of body weight. By way of general guidance, unit doses for humans range from 1 mg to 3000 mg per day. Preferably, the unit dose range is from 1 to 500 mg administered one to six times a day, and even more preferably from 10 mg to 500 mg, once a day. Compounds provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches.

The compositions may conveniently be administered in unit dosage form and may be prepared by any of the methods well-known in the pharmaceutical art, for example, as described in *Remington: The Science and Practice of Pharmacy*, 20$^{th}$ ed.; Gennaro, A. R., Ed.; Lippincott Williams & Wilkins: Philadelphia, Pa., 2000.

Preferred formulations include pharmaceutical compositions in which a compound of the present invention is formulated for oral or parenteral administration.

For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate, or talc in any combination.

Liquid preparations for parenteral administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

The invention is further illustrated but not restricted by the description in the following examples.

Representative compounds of the invention are summarized in the table below:

| CHEMISTRY | Preparation Procedure |
|---|---|
| (structure) | Ex 5a/E |

-continued
| CHEMISTRY | Preparation Procedure |
|---|---|
| 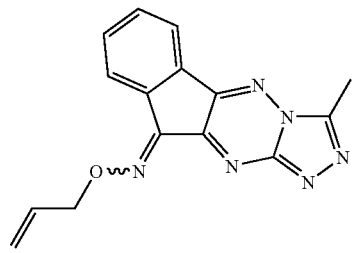 | Ex 5b/E |
| 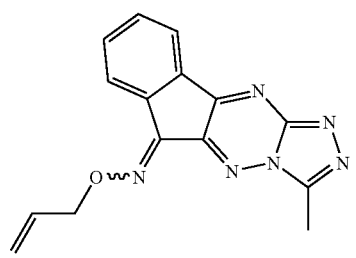 | Ex 5c/E |
| 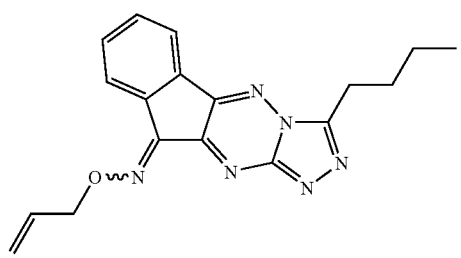 | Ex 5d/E |
| 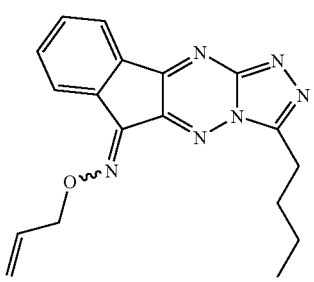 | Ex 5e/E |
| 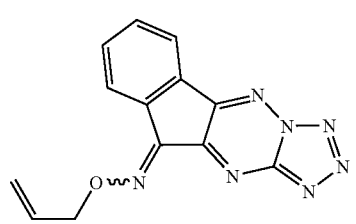 | Ex 6 |
| 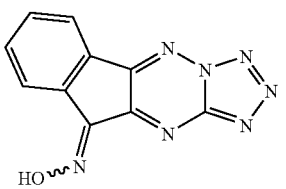 | Ex 7 |

| CHEMISTRY | Preparation Procedure |
|---|---|
| 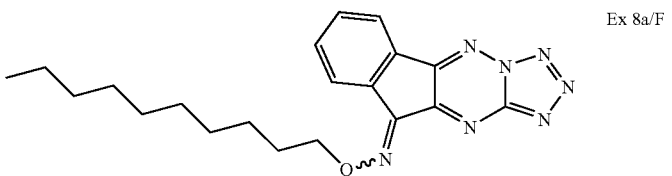 | Ex 8a/F |
| 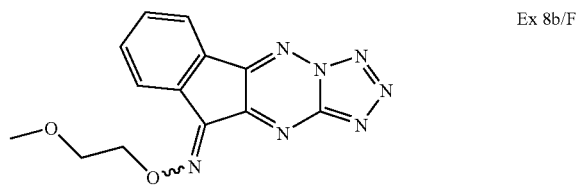 | Ex 8b/F |
| 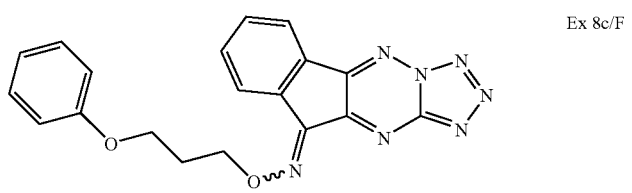 | Ex 8c/F |
| 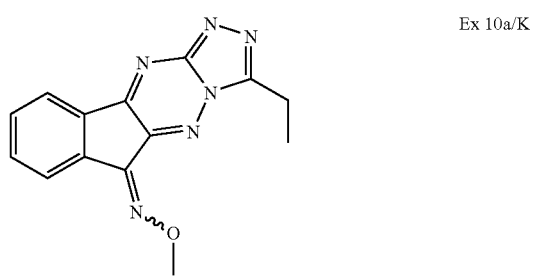 | Ex 10a/K |
| 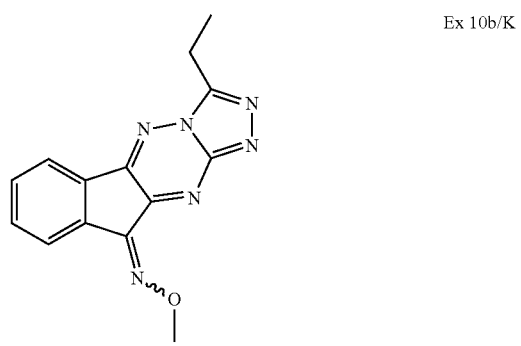 | Ex 10b/K |
| 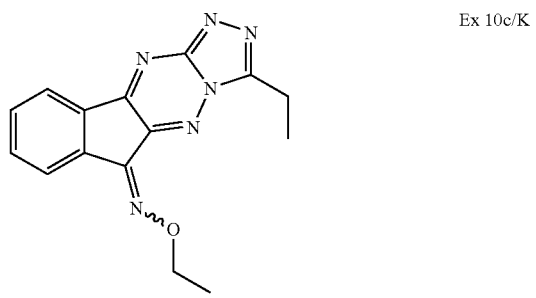 | Ex 10c/K |

-continued
| CHEMISTRY | Preparation Procedure |
|---|---|
| 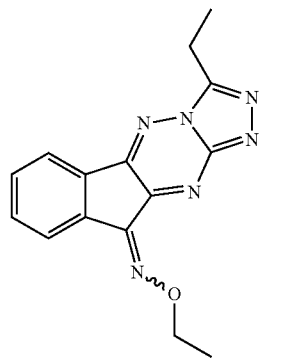 | Ex 10d/K |
| 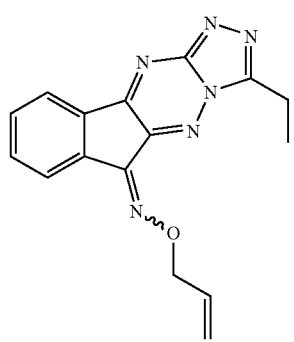 | Ex 10e/K |
| 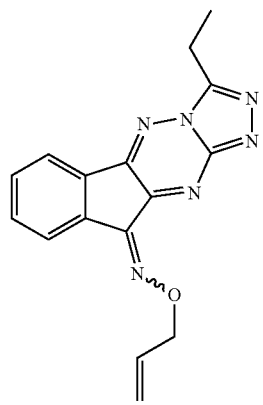 | Ex 10f/K |
| 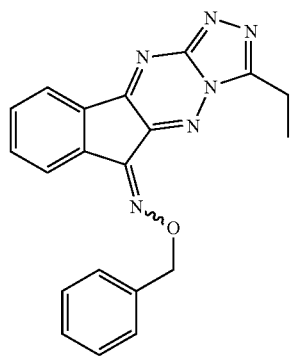 | Ex 10g/K |

| CHEMISTRY | Preparation Procedure |
|---|---|
| (structure) | Ex 10h/K |
| (structure) | Ex 11 |
| (structure) | Ex 12 |
| (structure) | Ex 13 |
EXPERIMENTAL
Representative compounds of the invention can be synthesized according to the following procedures:
General Procedure A: Synthesis of pentaaza-cyclopenta[b]fluoren-9-one:
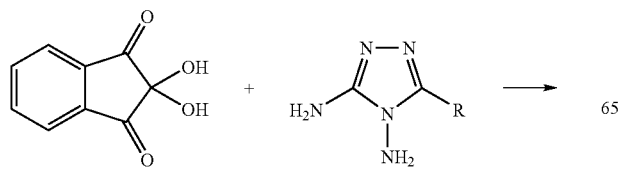

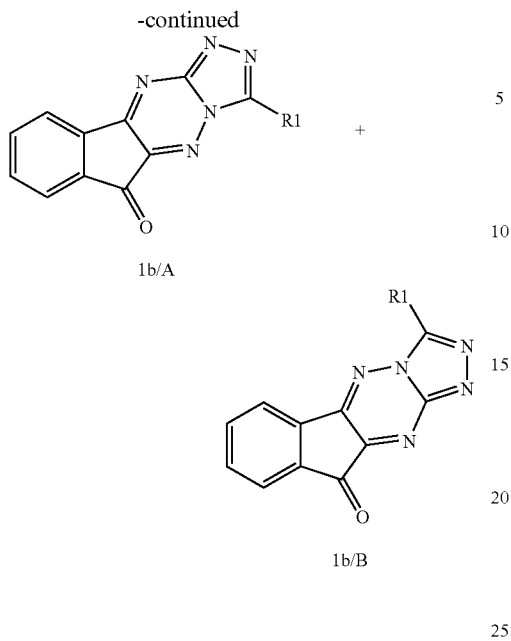

1b/A b R1 = Me

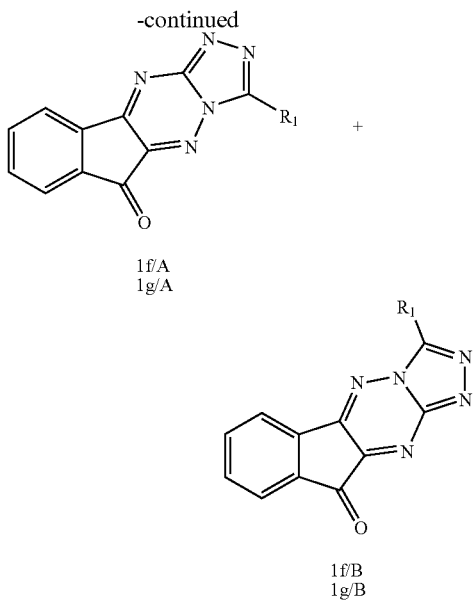

1f/A
1g/A

1f/B
1g/B f R1 = Bu
g R1 = Et

A mixture of R1-substituted (1,2,4)-triazole-3,4-diamine (8.8 mmol) and ninhydrin (1.57 g, 8.8 mmol) in EtOH (10 ml) and AcOH (1.5 ml) was refluxed for 2-16 hours. The solvent was removed under reduced pressure and the residue was dissolved in EtOAc, washed with saturated $K_2CO_3$ and brine. The organic phase was dried over $Na_2SO_4$, filtered and the solvents removed by evaporation under reduced pressure. The crude was purified as follows: silica gel flash chromatography (toluene/MeOH 95:5 to 8:2 or $CH_2Cl_2$/EtOAc 9:1 to 1:1) for the purification of the regioisomeric mixture, then neutral alumina (grade II) flash chromatography ($CH_2Cl_2$/EtOAc 7:3 to $CH_2Cl_2$/MeOH 1:1+5% HCOOH or AcOH) for the separation of the regioisomers.

1-Methyl-2,3,4,10,10a-pentaaza-cyclopenta[b]fluoren-9-one (1b/A)

Prepared according to the general procedure A in 13% yield as yellow solid. $^1$H NMR (300 MHz, DMSO $d_6$): δ 8.23 (d, 1H), 8.02 (m, 2H), 7.89 (ddd, 1H), 2.72 (s, 3H). ESI$^+$MS: calcd for $C_{12}H_7N_5O$: 237.22; found: 238.2 (MH$^+$).

3-Methyl-1,2,3a,4,10-pentaaza-cyclopenta[b]fluoren-9-one (1b/B)

Prepared according to the general procedure A in 30% yield as yellow solid. $^1$H NMR (300 MHz, DMSO $d_6$): δ 8.16 (d, 1H), 8.05-7.95 (m, 2H), 7.85 (ddd, 1H), 2.77 (s, 3H). ESI$^+$MS: calcd for $C_{12}H_7N_5O$: 237.22; found: 238.2 (MH$^+$).

General Procedure B: Synthesis of pentaaza-cyclopenta[b]fluoren-9-one:

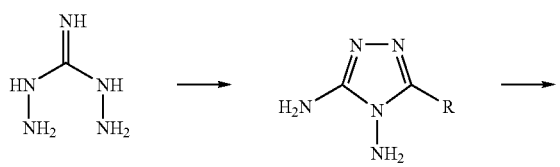

The preparation of diaminotriazoles follows the procedure reported in Eur. J. Med. Chem.-Chim. Ther. 1986, 21, 235.

A mixture of diaminoguanidine hydrochloride (1 g, 8 mmol) in an excess (10 g) of the appropriate carboxylic acid was stirred and heated at 120-130° C. for 12-24 hours. The solution was cooled to room temperature and HCl 37% (10 ml) was added. The mixture was refluxed for 2-3 hours and then concentrated to dryness in vacuo. The obtained crude was washed with $Et_2O$ (×3) and used without any further purification.

For the condensation between the crude diaminotriazole and ninhydrin, see the General procedure A.

1-Butyl-2,3,4,10,10a-pentaaza-cyclopenta[b]fluoren-9-one (1f/A)

Prepared according to the general procedure B in 6% yield as yellow solid. $^1$H NMR (300 MHz, DMSO $d_6$): δ 8.23 (d, 1H), 8.02 (m, 2H), 7.89 (ddd, 1H), 3.10 (dd, 2H), 1.81 (m, 2H), 1.42 (m, 2H), 0.94 (t, 3H). ESI$^+$MS: calcd for $C_{15}H_{13}N_5O$: 279.30; found: 280.2 (MH$^+$).

3-Butyl-1,2,3a,4,10-pentaaza-cyclopenta[b]fluoren-9-one (1f/B)

Prepared according to the general procedure B in 10% yield as yellow solid. $^1$H NMR (300 MHz, DMSO $d_6$): δ 8.16 (d,1H), 7.99 (m, 2H), 7.85 (dd,1H), 3.16 (dd, 2H), 1.87 (m, 2H), 1.44 (m, 2H), 0.96 (t, 3H). ESI$^+$MS: calcd for $C_{15}H_{13}N_5O$: 279.30; found: 280.3 (MH$^+$).

1-Ethyl-2,3,4,10,10a-pentaaza-cyclopenta[b]fluoren-9-one (1g/A)

Prepared according to the general procedure B in 48% yield as yellow solid. $^1$H NMR (300 MHz, CDCl$_3$): δ 8.21 (d, 1H), 8.00 (d, 1H), 7.90 (ddd, 1H), 7.77(ddd, 1H), 3.21 (q, 2H), 1.49 (t, 3H). ESI$^+$MS: calcd for $C_{13}H_9N_5O$: 251.25; found: 252.1 (MH$^+$).

3-Ethyl-1,2,3a,4,10-pentaaza-cyclopenta[b]fluoren-9-one (1g/B)

Prepared according to the general procedure B in 32% yield as yellow solid. $^1$H NMR (300 MHz, CDCl$_3$): δ 8.12 (d, 1H), 8.02 (d, 1H), 7.88 (ddd, 1H), 7.75 (ddd, 1H), 3.25 (q, 2H), 1.53 (t, 3H). ESI⁺MS: calcd for C₁₃H₉N₅O: 251.25; found: 252.1 (MH⁺).

General Procedure E: Synthesis of O-alkyloxime derivatives of pentaaza-cyclopenta [b]fluoren-9-one:

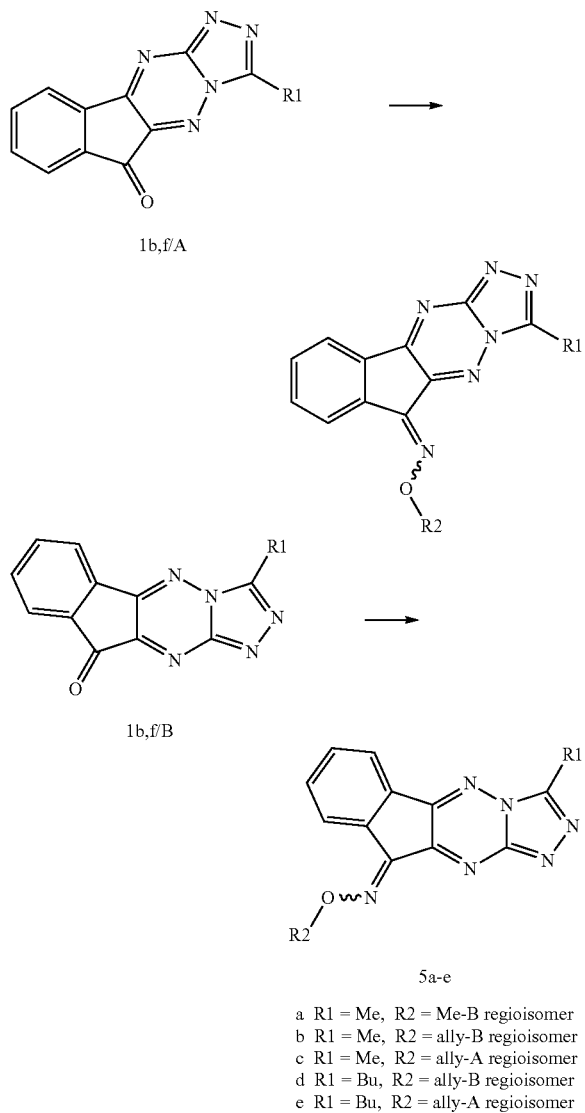

A suspension of 1 (1 mmol), O-alkyl-hydroxylamine hydrochloride (3 mmol) and molecular sieves in pyridine (10 ml) was heated to 60° C. for 2-12 h. The insoluble residue was filtered, the solvent evaporated and the crude purified by flash chromatography on silica gel (CH₂Cl₂/acetone 85:15 or toluene/MeOH 9:1 or petroleum spirit/EtOAc 1:1).

3-Methyl-1,2,3a,4,10-pentaaza-cyclopenta[b]fluoren-9-one O-methyl-oxime (5a)

Prepared according to the general procedure E from 1b/B in 55% yield as yellow solid as 2:1 E/Z mixture. ¹H NMR (300 MHz, DMSO d₆) (mixture of isomers): δ 8.43 (m, 1H), 8.16 (m, 1H), 7.81 (m, 2H), 4.34 (s, 3H), 2.75 (s, 3H). 8.05 (m, 1H), 7.92 (m, 1H), 7.72 (m, 2H), 4.30 (s, 3H), 2.75 (s, 3H). ESI⁺MS: calcd for C₁₃H₁₀N₆O: 266.26; found: 267.1 (MH⁺).

3-Methyl-1,2,3a,4,10-pentaaza-cyclopenta[b]fluoren-9-one O-allyl-oxime (5b)

Prepared according to the general procedure E from 1b/B in 65% yield as yellow solid as 1:1 E/Z mixture. ¹H NMR (300 MHz, CDCl₃) (mixture of isomers): δ 8.02 (d, 1H), 7.95 (d, 1H), 7.75-7.56 (m, 2H), 6.26-6.08 (m, 1H), 5.50 (dd, 1H), 5.35 (d, 1H), 5.05 (d, 2H), 2.86 (s, 3H). 8.49 (m, 1H), 8.13 (m, 1H), 7.77-7.56 (m, 2H), 6.26-6.08 (m, 1H), 5.50 (dd, 1H), 5.39 (d, 1H), 5.12 (d, 2H), 2.86 (s, 3H). ESI⁺MS: calcd for C₁₅H₁₂N₆O: 292.30; found: 293.1 (MH⁺).

1-Methyl-2,3,4,10,10a-pentaaza-cyclopenta[b]fluoren-9-one O-allyl-oxime (5c)

Prepared according to the general procedure E from 1b/A in 76% yield as yellow solid as 7:3 E/Z mixture. ¹H NMR (300 MHz, CDCl₃) (mixture of isomers): δ 8.16 (m, 1H), 7.95 (m, 1H), 7.77-7.60 (m, 2H), 6.26-6.08 (m, 1H), 5.54 (ddt, 1H), 5.37 (ddt, 1H), 5.04 (ddd, 2H), 2.84 (s, 3H). 8.49 (m, 1H), 8.26 (m, 1H), 7.77-7.60 (m, 2H), 6.26-6.08 (m, 1H), 5.49 (ddt, 1H), 5.40 (ddt, 1H), 5.09 (ddd, 2H), 2.88 (s, 3H). ESI⁺MS: calcd for C₁₅H₁₂N₆O: 292.30; found: 293.1 (MH⁺).

3-Butyl-1,2,3a,4,10-pentaaza-cyclopenta[b]fluoren-9-one O-allyl-oxime (5d)

Prepared according to the general procedure E from 1f/B in 93% yield as yellow solid as 6:4 E/Z mixture. ¹H NMR (300 MHz, CDCl₃) (mixture of isomers): δ 8.42 (m, 1H), 8.06 (m, 1H), 7.64 (m, 2H), 6.19-6.00 (m, 1H), 5.41 (m, 1H), 5.31 (m, 1H), 5.03 (ddd, 2H), 3.17 (dd, 2H), 1.88 (m, 2H), 1.43 (m, 2H), 0.93 (t, 3H). 7.96 (m, 1H), 7.87 (m, 1H), 7.55 (m, 2H), 6.19-6.00 (m, 1H), 5.41 (m, 1H), 5.26 (m, 1H), 4.97 (ddd, 2H), 3.17 (dd, 2H), 1.88 (m, 2H), 1.43 (m, 2H), 0.93 (t, 3H). ESI⁺MS: calcd for C₁₈H₁₈N₆O: 334.38; found: 335.1 (MH⁺).

1-Butyl-2,3,4,10,10a-pentaaza-cyclopenta[b]fluoren-9-one O-allyl-oxime (5e)

Prepared according to the general procedure E from 1f/A in 95% yield as yellow solid as 1:1 E/Z mixture. ¹H NMR (300 MHz, CDCl₃) (mixture of isomers): δ 8.45 (m, 1H), 8.22 (m, 1H), 7.69 (m, 2H), 6.22-6.02 (m, 1H), 5.45 (m, 1H), 5.35 (m, 1H), 5.05 (ddd, 2H), 3.21 (dd, 2H), 1.91 (m, 2H), 1.45 (m, 2H), 0.95 (t, 3H). 8.12 (m, 1H), 7.91 (m, 1H), 7.62 (m, 2H), 6.22-6.02 (m, 1H), 5.49 (m, 1H), 5.32 (m, 1H), 4.99 (ddd, 2H), 3.18 (dd, 2H), 1.91 (m, 2H), 1.45 (m, 2H), 0.95 (t, 3H). ESI⁺MS: calcd for C₁₈H₁₈N₆O: 334.38; found: 335.2 (MH⁺).

Synthesis of 1,2,3,3a,4,10-hexaaza-cyclopenta[b]fluoren-9-one O-allyl-oxime and/or its Corresponding Regioisomeric tetrazol (6):

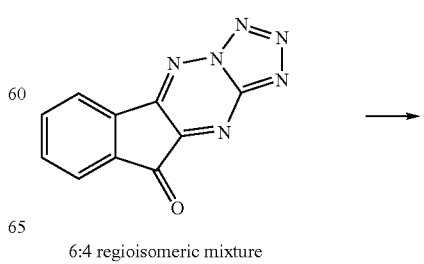

6:4 regioisomeric mixture

-continued

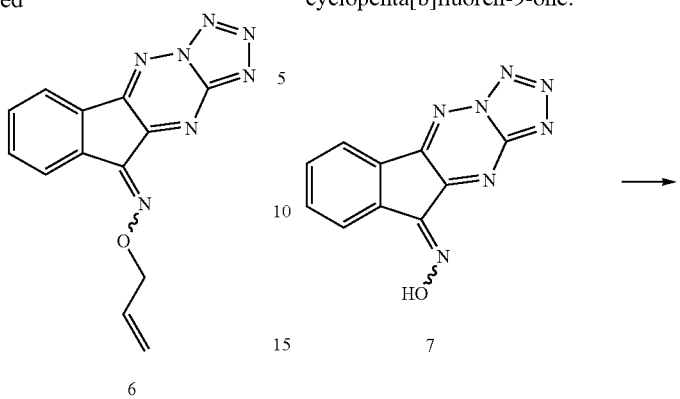

6

The compound was prepared according to the general procedure E from a 6:4 regioisomeric mixture of 1,2,3,3a,4,10-hexaaza-cyclopenta[b]fluoren-9-one (prepared from ninhydrin and tetrazole-1,5-diamine) in 89% yield as yellow solid as E/Z and regioisomeric mixture. $^1$H NMR (300 MHz, CDCl$_3$) (mixture of isomers): δ 8.47 (m, 1H), 8.22 (m, 1H), 7.84-7.58 (m, 2H), 6.23-6.03 (m, 1H), 5.46 (m, 1H), 5.37 (m, 1H), 5.13 (ddd, 2H). 8.19 (m, 1H), 7.98 (m, 1H), 7.84-7.58 (m, 2H), 6.23-6.03 (m, 1H), 5.46 (m, 1H), 5.34 (m, 1H), 5.06 (m, 2H). ESI$^+$MS: calcd for C$_{13}$H$_9$N$_7$O: 279.26; found: 280.2 (MH$^+$).

Synthesis of 1,2,3,3a,4,10-hexaaza-cyclopenta[b]fluoren-9-one oxime and/or its Corresponding Regioisomeric tetrazol (7):

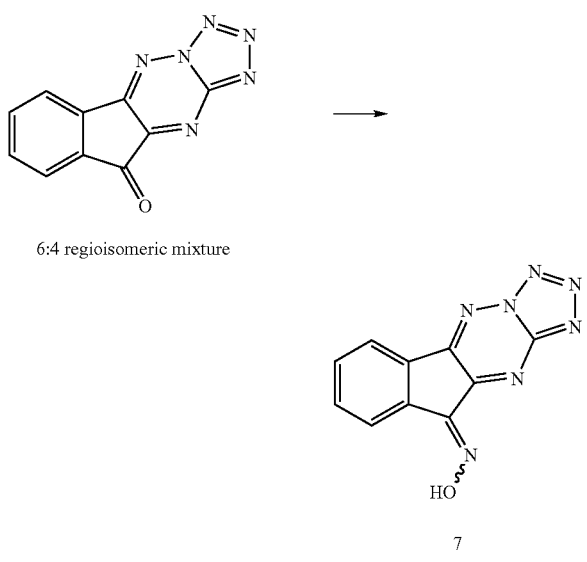

6:4 regioisomeric mixture

7

The compound was prepared according to the general procedure E from a 6:4 regioisomeric mixture of 1,2,3,3a,4,10-hexaaza-cyclopenta[b]fluoren-9-one (prepared from ninhydrin and tetrazole-1,5-diamine) in 44% yield as yellow solid as E/Z and regioisomeric mixture. $^1$H NMR (300 MHz, CDCl$_3$) (mixture of isomers): δ 13.87 (bs, 1H), 8.59 (m, 1H), 8.14 (m, 1H), 7.78-7.52 (m, 2H). 13.69 (bs, 1H), 8.05 (d, 1H), 7.91 (d, 1H), 7.78-7.52 (m, 2H). ESI$^+$MS: calcd for C$_{10}$H$_5$N$_7$O: 239.20; found: 240.1 (MH$^+$).

General Procedure F: Synthesis of O-alkyloxime of hexaaza-cyclopenta[b]fluoren-9-one:

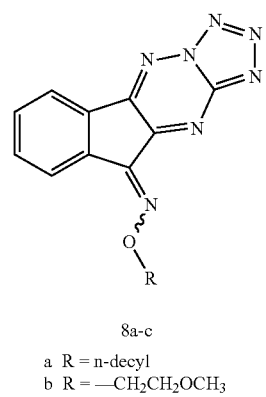

7

8a-c
a R = n-decyl
b R = —CH$_2$CH$_2$OCH$_3$
c R = —CH$_2$CH$_2$CH$_2$OPh

A mixture of 7 (48 mg, 0.20 mmol), alkyl bromide (0.6 mmol) and K$_2$CO$_3$ (55 mg, 0.4 mmol) in DMF (2 ml) was stirred at room temperature for 16 h, then the solvent was evaporated under reduced pressure. The crude was purified by flash chromatography (CH$_2$Cl$_2$ in variable mixture with MeOH or petroleum ether).

1,2,3,3a,4,10-Hexaaza-cyclopenta[b]fluoren-9-one O-decyl-oxime and/or its Corresponding Regioisomeric tetrazol (8a)

Prepared according to the general procedure F in 53% yield as yellow-green solid as E/Z and regioisomeric mixture. $^1$H NMR (300 MHz, CDCl$_3$) (mixture of isomers): δ 8.39 (m, 1H), 8.24 and 8.15 (m, 1H), 7.78-7.63 (m, 2H), 4.61-4.47 (m, 2H), 1.82 (m, 2H), 1.47-1.06 (m, 14H), 0.75 (m, 3H). ESI$^+$ MS: calcd for C$_{20}$H$_{25}$N$_7$O: 379.47; found: 380.2 (MH$^+$).

1,2,3,3a,4,10-Hexaaza-cyclopenta[b]fluoren-9-one O-(2-methoxy-ethyl)-oxime and/or its Corresponding Regioisomeric tetrazol_(8b)

Prepared according to the general procedure F in 29% yield as light brown solid as E/Z and regioisomeric mixture. $^1$H NMR (300 MHz, DMSO d$_6$) (mixture of isomers): δ 8.49 (m, 1H), 8.27 (m, 1H), 7.83-7.66 (m, 2H), 4.73 (m, 2H), 3.82 (m, 2H), 3.40 (s, 3H). 8.49 (m, 1H), 8.19 (m, 1H), 7.83-7.66 (m, 2H), 4.73 (m, 2H), 3.82 (m, 2H), 3.41 (s, 3H). ESI$^+$MS: calcd for C$_{13}$H$_{11}$N$_7$O$_2$: 297.28; found 298.0 (MH$^+$).

1,2,3,3a,4,10-Hexaaza-cyclopenta[b]fluoren-9-one O-(3-phenoxy-propyl)-oxime and/or its Corresponding Regioisomeric tetrazol (8c)

Prepared according to the general procedure F in 42% yield as yellow solid as E/Z and regioisomeric mixture. $^1$H NMR (300 MHz, CDCl$_3$) (mixture of isomers): δ 8.41 (m, 1H), 8.15 (m, 1H), 7.76-7.58 (m, 2H), 7.18 (m, 2H), 6.83 (m, 3H), 4.87-4.70 (m, 2H), 4.18-4.07 (m, 2H), 2.42-2.27 (m, 2H). 8.26 (m, 1H), 7.89 (d, 1H), 7.76-7.58 (m, 2H), 7.18 (m, 2H), 6.83 (m, 3H), 4.87-4.70 (m, 2H), 4.18-4.07 (m, 2H), 2.42-2.27 (m, 2H). ESI⁺MS: calcd for $C_{19}H_{15}N_7O_2$: 373.38; found: 374.1 (MH⁺).

General Procedure K: Synthesis of O-alkyloxime Derivatives of ethyl pentaaza-cyclopenta[b]fluoren-9-one:

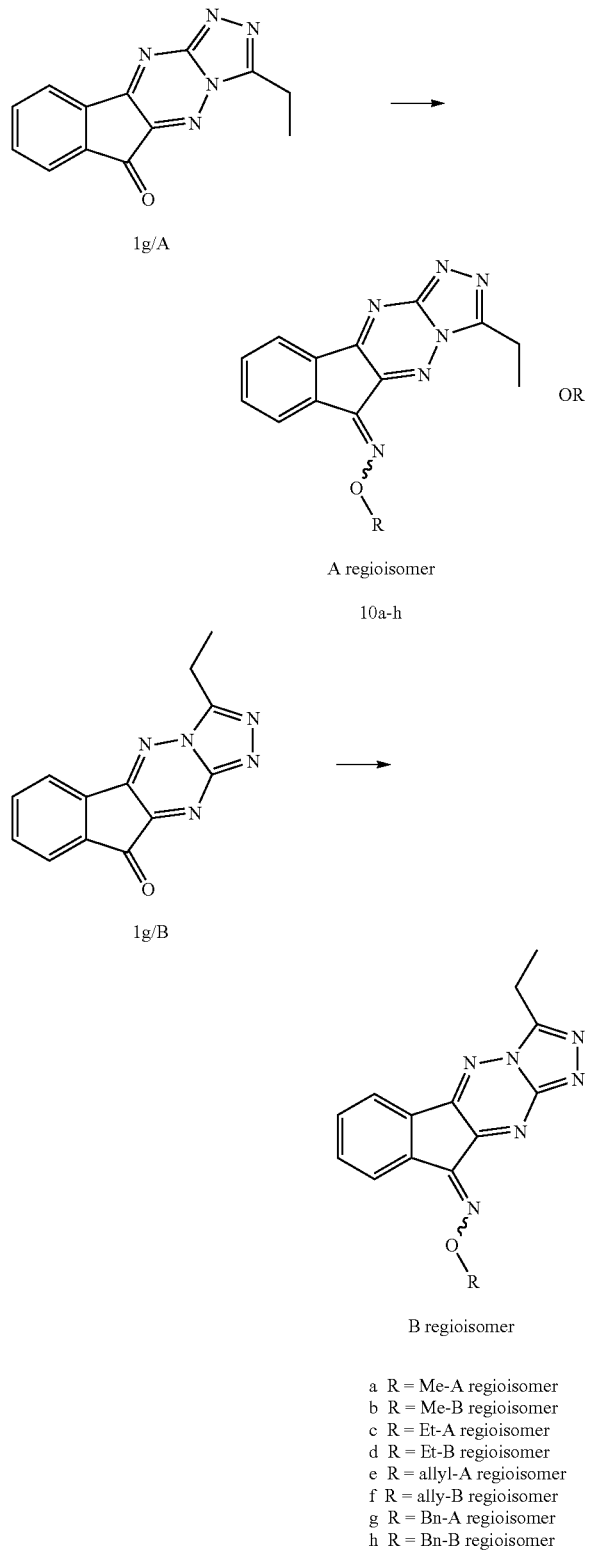

a  R = Me-A regioisomer
b  R = Me-B regioisomer
c  R = Et-A regioisomer
d  R = Et-B regioisomer
e  R = allyl-A regioisomer
f  R = ally-B regioisomer
g  R = Bn-A regioisomer
h  R = Bn-B regioisomer A suspension of 1g/A or 1g/B (1 mmol), O-alkyl-hydroxylamine hydrochloride (2 mmol) and molecular sieves in pyridine (10 ml) was heated to 60° C. for 2-3 h. The insoluble residue was filtered, the solvent evaporated and the crude purified by flash chromatography on silica gel.

1-Ethyl-2,3,4,10,10a-pentaaza-cyclopenta[b]fluoren-9-one O-methyl-oxime (10a)

Prepared according to the general procedure K (eluent: $CH_2Cl_2$/EtOAc/MeOH 80:17:3) from 1g/A in quantitative yield as yellow solid as 7:3 E/Z mixture. ¹H NMR (300 MHz, CDCl₃): δ 8.47 (m, 1H), 8.27 (m, 1H), 7.73 (m, 1H), 7.66 (m, 1H), 4.41 (s, 3H), 3.28 (q, 2H), 1.55 (t, 3H) and 8.17 (m, 1H), 7.96 (m, 1H), 7.73 (m, 1H), 7.63 (m, 1H), 4.37 (s, 3H), 3.25 (q, 2H), 1.55 (t, 3H). ESI⁺MS: calcd for $C_{14}H_{12}N_6O$: 280.29; found: 281.1 (MH⁺).

3-Ethyl-1,2,3a,4,10-pentaaza-cyclopenta[b]fluoren-9-one O-methyl-oxime (10b)

Prepared according to the general procedure K (eluent: $CH_2Cl_2$/EtOAc/MeOH 80:17:3) from 1g/B in quantitative yield as yellow solid as 7:3 E/Z mixture. ¹H NMR (300 MHz, CDCl₃): δ 8.50 (m, 1H), 8.17 (m, 1H), 7.63 (m, 2H), 4.45 (s, 3H), 3.30 (q, 2H), 1.57 (t, 3H) and 8.07 (d, 1H), 7.98 (d, 1H), 7.68 (ddd, 1H), 7.64 (ddd, 1H), 4.41 (s, 3H), 3.29 (q, 2H), 1.59 (t, 3H). ESI⁺MS: calcd for $C_{14}H_{12}N_6O$: 280.29; found: 281.1 (MH⁺).

1-Ethyl-2,3,4,10,10a-pentaaza-cyclopenta[b]fluoren-9-one O-ethyl-oxime (10c)

Prepared according to the general procedure K (eluent: $CH_2Cl_2$/EtOAc/MeOH 70:25:5) from 1g/A in quantitative yield as yellow solid as 6:4 E/Z mixture. ¹H NMR (300 MHz, CDCl₃): δ 8.17 (m, 1H), 7.96 (m, 1H), 7.73 (m, 1H), 7.65 (ddd, 1H), 4.60 (q, 2H), 3.26 (q, 2H), 1.55 (t, 3H), 1.55 (t, 3H) and 8.47 (m, 1H), 8.27 (m, 1H); 7.72 (m, 1H), 7.63 (ddd, 1H), 4.66 (q, 2H), 3.30 (q, 2H), 1.54 (t, 3), 1.51 (t, 3H). ESI⁺MS: calcd for $C_{15}H_{14}N_6O$: 294.32; found: 295.1 (MH⁺).

3-Ethyl-1,2,3a,4,10-pentaaza-cyclopenta[b]fluoren-9-one O-ethyl-oxime (10d)

Prepared according to the general procedure K (eluent: $CH_2Cl_2$/EtOAc/MeOH 70:25:5) from 1g/B in quantitative yield as yellow solid as 1:1 E/Z mixture. ¹H NMR (300 MHz, CDCl₃): δ 8.49 (m, 1H), 8.13 (m, 1H), 7.70 (m, 1H), 7.62 (m, 1H), 4.69 (q, 2H), 3.27 (q, 2H), 1.58-1.48 (m, 6H), and 8.03 (m, 1H), 7.96 (m, 1H), 7.70 (m, 1H), 7.62 (m, 1H), 4.62 (q, 2H), 3.27 (q, 2H), 1.58-1.48 (m, ESI⁺MS: calcd for $C_{15}H_{14}N_6O$: 294.32; found: 295.1 (MH⁺).

1-Ethyl-2,3,4,10,10a-pentaaza-cyclopenta[b]fluoren-9-one O-allyl-oxime (10e)

Prepared according to the general procedure K (eluent: $CH_2Cl_2$/EtOAc/MeOH 80:16:4) from 1g/A in quantitative yield as yellow solid as 6:4 E/Z mixture. ¹H NMR (300 MHz, CDCl₃): δ 8.17 (d, 1H), 7.95 (d, 1H), 7.65 (m, 2H), 6.26-6.07 (m, 1H), 5.54 (m, 1H), 5.37 (m, 1H), 5.04 (ddd, 2H), 3.26 (q, 2H), 1.54 (m, 3H) and 8.49 (d, 1H), 8.27 (d, 1H), 7.73 (m, 2H), 6.26-6.07 (m, 1H), 5.49 (m, 1H), 5.40 (m, 1H), 5.09 (ddd, 2H), 3.26 (m, 2H), 1.54 (m, 3H). ESI⁺MS: calcd for $C_{16}H_{14}N_6O$: 306.33; found: 307.1 (MH⁺).

3-Ethyl-1,2,3a,4,10-pentaaza-cyclopenta[b]fluoren-9-one O-allyl-oxime (10f)

Prepared according to the general procedure K (eluent: $CH_2Cl_2$/EtOAc/MeOH 80:17:3) from 1g/B in 96% yield as yellow solid as 65:35 E/Z mixture. ¹H NMR (300 MHz, CDCl₃): δ 8.50 (m, 1H), 8.14 (m, 1H), 7.71 (m, 1H), 7.65 (m, 1H), 6.26-6.09 (m, 1H), 5.53 (m, 1H), 5.39 (m, 1H), 5.12 (ddd, 2H), 3.27 (q, 2H), 1.55 (t, 3H) and 8.04 (m, 1H), 7.95

(m, 1H), 7.71 (m, 1H), 7.61 (m, 1H), 6.26-6.09 (m, 1H), 5.47 (m, 1H), 5.36 (m, 1H), 5.106 (ddd, 2H), 3.27 (q, 2H), 1.56 (t, 3H). ESI⁺MS: calcd for $C_{16}H_{14}N_6O$: 306.33; found: 307.2 (MH⁺).

1-Ethyl-2,3,4,10,10a-pentaaza-cyclopenta[b]fluoren-9-one O-benzyl-oxime (10g)

Prepared according to the general procedure K (eluent: CH₂Cl₂/EtOAc/MeOH 80:17:3) from 1g/A in 86% yield as yellow solid as 65:35 E/Z mixture. ¹H NMR (300 MHz, CDCl₃): δ 8.16 (m, 1H), 7.96 (m, 1H), 7.70 (m, 1H), 7.65 (m, 1H), 7.52 (m, 2H), 7.41 (m, 3H), 5.58 (s, 2H), 3.21 (q, 2H), 1.49 (t, 3H) and 8.43 (m, 1H), 8.26 (m, 1H), 7.70 (m, 1H), 7.65 (m, 1H), 7.52 (m, 2H), 7.41 (m, 3H), H), 5.62 (s, 2H), 3.29 (q, 2H), 1.56 (t, 3H). ESI⁺MS: calcd for $C_{20}H_{16}N_6O$: 356.39; found: 357.1 (MH⁺).

3-Ethyl-1,2,3a,4,10-pentaaza-cyclopenta[b]fluoren-9-one O-benzyl-oxime (10h)

Prepared according to the general procedure K (eluent: CH₂Cl₂/EtOAc/MeOH 80:17:3) from 1g/B in 99% yield as yellow solid as 6:4 E/Z mixture. ¹H NMR (300 MHz, CDCl₃): δ 8.44 (m, 1H), 8.13 (m, 1H), 7.67 (m, 1H), 7.61 (m, 1H), 7.52 (m, 2H), 7.46-7.29 (m, 3H), 5.64 (s, 2H), 3.62 (q, 2H), 1.55 (t, 3H) and 8.01 (m, 1H), 7.92 (m, 1H), 7.70 (m, 1H), 7.65 (m, 1H), 7.52 (m, 2H), 7.41 (m, 3H), 5.59 (s, 2H), 3.29 (q, 2H), 1.56 (t, 3H). ESI⁺MS: calcd for $C_{20}H_{16}N_6O$: 356.39; found: 357.1 (MH⁺).

Synthesis of [1-Ethyl-2,3,4,10,10a-pentaaza-cyclopenta[b]fluoren-9-ylidene]-phenyl-amine (11):

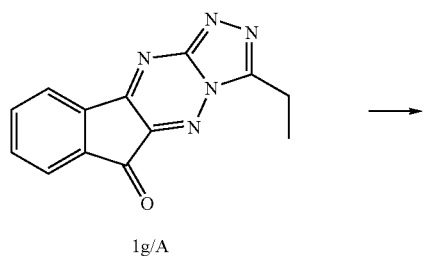

1g/A

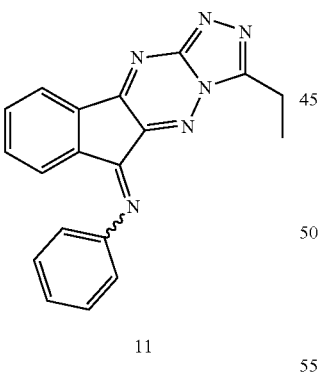

11

To a suspension of 1g/A (200 mg, 0.79 mmol) and molecular sieves in toluene (4 ml), aniline (72 μl, 0.79 mmol) was added. The mixture was stirred at 130° C. for 4 h, then the solvent was evaporated and he crude purified by flash chromatography (CH₂Cl₂/EtOAc/MeOH 80:18:2), affording 11 (231 mg, 90%) as orange solid in diastereoisomeric ratio 1:1.

¹H NMR (300 MHz, CDCl₃): δ 8.28 (d, 1H), 7.70 (ddd, 1H), 7.56-7.26 (m, 6H), 6.91 (d, 1H), 3.34 (q, 2H), 1.58 (t, 3H) and 8.22 (m, 2H), 7.81 (m, 2H), 7.47 (m, 1H), 7.07 (m, 4H), 2.80 (q, 2H), 1.21 (t, 3H). ESI+MS: calcd for $C_{19}H_{14}N_6$: 326.36; found: 327.2 (MH⁺).

(1,2,3,3a,4,10-Hexaaza-cyclopenta[b]fluoren-9-ylideneaminooxy)-acetic acid ethyl ester and/or its Corresponding Regioisomeric tetrazol (12)

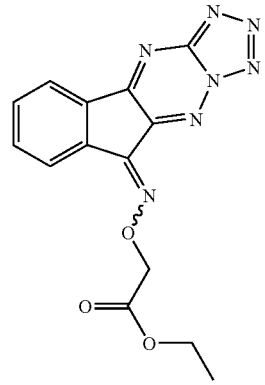

(mixture of isomers)

A mixture of oxime 7 (560 mg, 2.34 mmol) and cesium carbonate (1.54 g, 4.68 mmol) were stirred in DMF (12 ml) for 5 min. Ethyl bromoacetate (1.2 g, 7.02 mmol) was added dropwise, and at the end of the addition, the deeply colored mixture was stirred for 3 h at room temperature. The solvent was evaporated, and the crude product dissolved in dichloromethane. After filtration over a pad of silice, evaporation, recrystallisation with cyclohexane/ethyl acetate and trituration with cyclohexane, 717 mg (94%) of compound 12 was obtained as a green powder.

¹H-NMR (400 MHz, d₆-DMSO) (mixture of isomers): δ(ppm)=1.28 (m, 3H); 4.21 (m, 2H); 5.28 (m, 2H); 7.70-8.60 (m, 4H). LC-MS (ES): m/z=651 (2M+H⁺), 326 (M+H⁺).

(1,2,3,3a,4,10-Hexaaza-cyclopenta[b]fluoren-9-ylideneaminooxy)-acetate Lithium salt and/or its Corresponding Regioisomeric tetrazol (13)

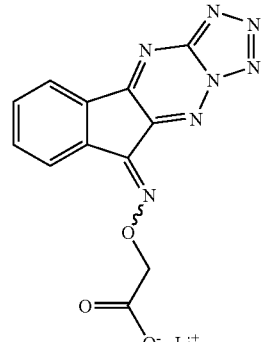

(mixture of isomers)

A solution of ester 12 (700 mg; 2.15 mmol) and LiOH (451 mg, 10.75 mmol) in 12 ml methanol were stirred for 2 h at room temperature. The deeply coloured mixture was cooled to −20° C., and after 1 h, the predpitate formed filtered and washed with cold methanol to leave 380 mg (59%) of compound 13 as a green solid.

¹H-NMR (400 MHz, D₂O) (mixture of isomers): δ(ppm)= 4.8 (s, 2H); 7.40-8.40 (m, 4H). LC-MS (ES): m/z=296 (M−H⁺).

Representative Cysteine Proteases

USP5 Activity Assay

USP5 was diluted in USP buffer (50 mM Tris HCl; 0.5 mM EDTA; 5 mM DTT; 0.01% Triton X-100; Bovine Serum Albumin 0.05 mg.ml$^{-1}$ pH7.6). Compounds stocks (100 mM) were stored at –20° C. in DMSO. Compounds were tested at the following final concentrations: 100 µM; 33.3 µM; 11.1 µM; 3.7 µM; 1.23 µM; 412 nM; 137 nM; 45.7 nM; 15.2 nM; 5 nM.

Reactions were performed as duplicates in Black LJL 96 well plates (HE microplates; Molecular Devices; 20 µl final reaction volume). The substrate concentration for USP5 was 400 nM Ub-AMC (Boston Biochem). The concentrations of the enzyme (USP5) in specificity assays was 300 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/–compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values+/–standard deviation) were analyzed as % of control (no compound) and plotted as percentage versus the Log of the compound concentration using GraphPad (Prism). Data were fitted to a sigmoidal model (variable slope).

Cloning & Purification of USP7

The cDNA encoding USP7 was obtained by PCR amplification from placenta mRNA. USP7 cDNA was subcloned by PCR into a baculovirus expression vector (pFastBac-HT; Invitrogen). A cDNA encoding a mutated USP7 was generated by mutagenic PCR. The corresponding protein encodes a cysteine to alanine substitution at residue 223. The sequences were ascertained by sequencing of the entire open reading frame. Bacmids encoding USP7 were generated following DH10bac transposition. The corresponding bacmids were transfected into insect cells (Sf9). Viruses were recovered from culture supernatant and amplified twice. Insect cells (Sf9 or High Five; Invitrogen) were infected for 72 hours. Total cell lysates were harvested and lyzed in lysis buffer (Tris HCl 50 mM pH7.6; 0.75% NP40; 500 mM NaCl; 10% glycerol; 1 mM DTT; 10 mM imidazole; Protease Inhibitor Cocktail; AEBSF 20 µg.ml$^{-1}$; Aprotinin 10 µg.ml$^{-1}$). Proteins were affinity purified on metal affinity resins (Talon Metal affinity resin; BD Biosciences). Bound materials were extensively washed in wash buffer (50 mM Sodium Phosphate pH7.0; 300 mM NaCl; 10 mM imidazole; 0.5% Triton X-100; 10% glycerol) and eluted from the resin in 250 mM imidazole-containing wash buffer. Proteins were dialyzed in dialysis buffer (Tris HCl pH 7.6 20 mM; NaCl 200 mM; DTT 1 mM; EDTA 1 mM; 10% Glycerol). Proteins purifications were analyzed on 4-12% NuPAGE (Invitrogen).

USP7 Activity Assay

USP7 was diluted in USP buffer (50 mM Tris HCl; 0.5 mM EDTA; 5 mM DTT; 0.01% Triton X-100; Bovine Serum Albumin 0.05 mg.ml$^{-1}$ pH7.6). Compounds stocks (100 mM) were stored at –20° C. in DMSO. Compounds were tested at the following final concentrations: 100 µM; 33.3 µM; 11.1 µM; 3.7 µM; 1.23 µM; 412 nM; 137 nM; 45.7 nM; 15.2 nM; 5 nM.

Reactions were performed as duplicates in Black LJL 96 well plates (HE microplates; Molecular Devices; 20 µl final reaction volume). The substrate concentration for USP7 was 400 nM Ub-AMC (*Chem. Biol.*, 2003, 10, p. 837-846) (Boston Biochem). The concentrations of the enzyme (USP7) in specificity assays was 152 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/–compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values+/–standard deviation) were analyzed as % of control (no compound) and plotted as percentage versus the Log of the compound concentration using GraphPad (Prism). Data were fitted to a sigmoidal model (variable slope).

Cloning & Purification of USP8

The cDNA encoding USP8 was obtained by PCR amplification from placenta mRNA. USP8 cDNA was subcloned by PCR into a baculovirus expression vector (pFastBac-HT; Invitrogen). A cDNA encoding a mutated USP8 was generated by mutagenic PCR. The corresponding protein encodes a cysteine to alanine substitution at residue 786. The sequences were ascertained by sequencing of the entire open reading frame. Bacmids encoding USP7 were generated following DH10bac transposition. The corresponding bacmids were transfected into insect cells (Sf9). Viruses were recovered from culture supernatant and amplified twice. Insect cells (Sf9 or High Five; Invitrogen) were infected for 72 hours. Total cell lysates were harvested and lyzed in lysis buffer (Tris HCl 50 mM pH7.6; 0.75% NP40; 500 mM NaCl; 10% glycerol; 1 mM DTT; 10 mM imidazole; Protease Inhibitor Cocktail; AEBSF 20 µg.ml$^{-1}$; Aprotinin 10 µg.ml$^{-1}$). Proteins were affinity purified on metal affinity resins (Talon Metal affinity resin; BD Biosciences). Bound materials were extensively washed in wash buffer (50 mM Sodium Phosphate pH 7.0; 300 mM NaCl; 10 mM imidazole; 0.5% Triton X-100; 10% glycerol) and eluted from the resin in 250 mM imidazole-containing wash buffer. Proteins were dialyzed in dialysis buffer (Tris HCl pH 7.6 20 mM; NaCl 200 mM; DTT 1 mM; EDTA 1 mM; 10% Glycerol). Proteins purifications were analyzed on 4-12% NuPAGE (Invitrogen).

USP8 Activity Assay

USP8 was diluted in USP buffer (50 mM Tris HCl; 0.5 mM EDTA; 5 mM DTT; 0.01% Triton X-100; Bovine Serum Albumin 0.05 mg.ml$^{-1}$ pH8.8). Compounds stocks (100 mM) were stored at –20° C. in DMSO. Compounds were tested at the following final concentrations: 100 µM; 33.3 µM; 11.1 µM; 3.7 µM; 1.23 µM; 412 nM; 137 nM; 45.7 nM; 15.2 nM; 5 nM.

Reactions were performed as duplicates in Black LJL 96 well plates (HE microplates; Molecular Devices; 20 µl final reaction volume). The substrate concentration for USP8 was 400 nM Ub-AMC (Boston Biochem). The concentrations of the enzyme (USP8) in specificity assays was 630 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/–compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values±standard deviation) were analyzed as % of control (no compound) and plotted as percentage versus the Log of the compound concentration using GraphPad (Prism). Data were fitted to a sigmoidal model (variable slope).

UCH-L3 Activity Assay

Uch-L3 was diluted in USP buffer (50 mM Tris HCl; 0.5 mM EDTA; 5 mM DTT; 0.01% Triton X-100; Bovine Serum Albumin 0.05 mg.ml$^{-1}$ pH7.6). Compounds stocks (100 mM) were stored at −20° C. in DMSO. Compounds were tested at the following final concentrations: 100 µM; 33.3 µM; 11.1 µM; 3.7 µM; 1.23 µM; 412 nM; 137 nM; 45.7 nM; 15.2 nM; 5 nM.

Reactions were performed as duplicates in Black LJL 96 well plates (HE microplates; Molecular Devices; 20 µl final reaction volume). The substrate concentration for Uch-L3 was 400 nM Ub-AMC (Boston Biochem). The concentration of the enzyme (Uch-L3) in specificity assays was 13 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/−compounds) diluted in assay buffer. Reactions were incubated for 60 minutes at 37° C. Reactions were stopped by adding acetic acid (100 mM final). Readings were performed on a Pherastar Fluorescent Reader (BMG). Δ Emission 380 nm; δ Excitation=460 nm. Data (mean values+/−standard deviation) were analyzed as % of control (no compound) and plotted as percentage versus the Log of the compound concentration using GraphPad (Prism). Data were fitted to a sigmoidal model (variable slope).

Caspase 3 Activity Assay

Caspase 3 was diluted in Caspase 3 buffer (100 mM Hepes pH 7.5; 10% sucrose; 0.1% CHAPS). Compounds stocks (100 mM) were stored at −20° C. in DMSO. Compounds were tested at the following final concentrations: 100 µM; 33.3 µM; 11.1 µM; 3.7 µM; 1.23 µM; 412 nM; 137 nM; 45.7 nM; 15.2 nM; 5 nM. Reactions were performed as duplicates in Black LJL 96 well plates (HE microplates; Molecular Devices; 20 µl final reaction volume). The substrate concentration for caspase 3 specificity assay was 500 nM (Ac-DEVD-AMC; Promega). The concentration of the enzyme (Caspase 3) in specificity assays was 3.2 nM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/−compounds) diluted in assay buffer. Reactions were incubated for 60 minutes at 37° C. Reactions were stopped by adding acetic acid(100 mM final). Readings were performed on a Pherastar Fluorescent Reader (BMG). δ Emission 380 nm; δ Excitation=460 nm. Data (mean values+/−standard deviation) were analyzed as % of control (no compound) and plotted as percentage versus the Log of the compound concentration using GraphPad (Prism). Data were fitted to a sigmoidal model (variable slope).

Cathepsin B Activity Assay

Cathepsin B was diluted in Cathepsin B buffer (20 mM Tris HCl pH 6.8; 1 mM EDTA; 1 mM DTT). Compounds stocks (100 mM) were stored at −20° C. in DMSO. Compounds were tested at the following final concentrations: 100 µM; 33.3 µM; 11.1 µM; 3.7 µM; 1.23 µM; 412 nM; 137 nM; 45.7 nM; 15.2 nM; 5 nM. Reactions were performed as duplicates in Black LJL 96 well plates (HE microplates; Molecular Devices; 20 µl final reaction volume). The substrate concentration for cathepsin B specificity assay was 36 µM (z-RR-AMC; Calbiochem).The concentration of the enzyme (Cathepsin B) in specificity assays was 3.6 nM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/−compounds) diluted in assay buffer. Reactions were incubated for 60 minutes at 37° C. Reactions were stopped by adding acetic acid (100 mM final). Readings were performed on a Pherastar Fluorescent Reader (BMG). δ Emission 380 nm; δ Excitation=460 nm. Data (mean values+/−standard deviation) were analyzed as % of control (no compound) and plotted as percentage versus the Log of the compound concentration using GraphPad (Prism). Data were fitted to a sigmoidal model (variable slope).

Cell Viability and Proliferation Methods

HCT116 Cell Viability and Proliferation Assay

HCT116 colon cancer cells were obtained from ATCC (American Type Culture Collection), and maintained in Mc Coy's 5A medium containing 10% FBS, 3 mM glutamine and 1% penicillin/streptomycin. Cells were incubated at 37° C. in a humidified atmosphere containing 5% $CO_2$.

Cell viability was assayed using the MTS technique in 96-well culture plates (CellTiter 96® Aqueous Non-Radioactive Cell Proliferation Assay, Promega) according to the manufacturer's instructions. MTS (3-(4,5-dimethylthiazol-2-yl)-5-(3-carboxymethoxyphenyl)-2-(4-sulfophenyl)-2H-tetrazolium) is a MTT-derived tetrazolium that is reduced in metabolically active cells into a soluble, cell-permeant formazan. The amount of formazan, detected by its absorbance at 492 nm is proportional to the number of living, metabolically active cells.

$10^3$ HCT116 cells were seeded per well. 24 hours later, the medium was changed and the cells treated in triplicate with the following concentrations of each compound: 10 µM-3.33 µM-1.11 µM-370 nM-123 nM-41 nM-14 nM and 5 nM. The compounds were diluted in 100% DMSO, whose final concentration on cells was kept at 0.5%.

Cells were incubated with the compounds for 72 hours, and their viability then assayed by the addition of MTS for 2 hours. Absorbance at 492 nm was measured directly from the 96-well culture plates. GI50 (Growth Inhibition 50) concentrations for each compound were calculated using a sigmoidal variable slope fit (Prism 4.0, Graphpad Softwares). Values represent mean of 3 independent experiments.

PC3 Cell Viability and Proliferation Assay

PC-3 prostate cancer cells were obtained from ATCC, and maintained in F-12K medium containing 7% FBS and 1% penicillin/streptomycin. Cells were incubated at 37° C. in a humidified atmosphere containing 5% $CO_2$.

Cell viability was assayed using the MTS technique in 96-well culture plates (CellTiter 96® Aqueous Non-Radioactive Cell Proliferation Assay, Promega) according to the manufacturer's instructions. MTS (3-(4,5-dimethyl-thiazol-2-yl)-5-(3-carboxymethoxyphenyl)-2-(4-sulfophenyl)-2H-tetrazolium) is a MTT-derived tetrazolium that is reduced in metabolically active cells into a soluble, cell-permeant formazan. The amount of formazan, detected by its absorbance at 492 nm is proportional to the number of living, metabolically active cells.

$2 \times 10^3$ PC3 cells were seeded per well. 24 hours later, the medium was changed and the cells treated in triplicate with the following concentrations of each compound: 10 µM-3.33 µM-1.11 µM-370 nM-123 nM-41 nM-14 nM and 5 nM. The compounds were diluted in 100% DMSO, whose final concentration on cells was kept at 0.5%.

Cells were incubated with the compounds for 72 hours, and their viability then assayed by the addition of MTS for 2 hours. Absorbance at 492 nm was measured directly from the 96-well culture plates. GI50 (Growth Inhibition 50) concentrations for each compound were calculated using a sigmoidal variable slope fit (Prism 4.0, Graphpad Softwares). Values represent mean of 3 independent experiments.

RESULTS

1. Inhibition of cysteine protease activities

| Experimental N° | USP5 | Experimental N° | USP7 |
|---|---|---|---|
| 5a | 1.8 µM | 5a | 4 µM |
| 5b | 1.15 µM | 5b | 3.14 µM |
| 5d | 1.42 µM | 5d | 5.35 µM |
| 6 | 0.175 µM | 6 | 0.305 µM |
| 7 | 0.264 µM | 7 | 0.657 µM |
| 8a | 54 µM | 8b | 0.470 µM |
| 8b | 0.226 µM | 8c | 1.78 µM |
| 8c | 0.470 µM | 10b | 4.84 µM |
| 10f | 1.2 µM | 10d | 3.11 µM |
| 12 | 0.131 µM | 10f | 3.25 µM |
| 13 | 0.215 µM | 10h | 7.28 µM |
|  |  | 12 | 0.307 µM |
|  |  | 13 | 0.415 µM |

| Experimental N° | USP8 | Experimental N° | UCH-L3 |
|---|---|---|---|
| 5a | 0.58 µM | 5a | 0.41 µM |
| 5b | 0.355 µM | 5b | 0.272 µM |
| 5c | 47.7 µM | 5c | 51 µM |
| 5d | 0.565 µM | 5d | 0.250 µM |
| 5e | 35 µM | 5e | 89 µM |
| 6 | 0.064 µM | 6 | 0.032 µM |
| 7 | 0.143 µM | 7 | 0.057 µM |
| 8a | 27.8 µM | 8a | 2.0 µM |
| 8b | 0.121 µM | 8b | 0.048 µM |
| 8c | 0.225 µM | 8c | 0.121 µM |
| 10b | 0.528 µM | 10f | 0.235 µM |
| 10d | 0.381 µM | 12 | 0.044 µM |
| 10f | 0.342 µM | 13 | 0.077 µM |
| 10h | 0.807 µM |  |  |
| 12 | 0.037 µM |  |  |
| 13 | 0.071 µM |  |  |

| Cathepsine B | |
|---|---|
| Experimental N° | cathepB |
| 5a | 2.6 µM |
| 5d | 6.7 µM |
| 6 | 0.300 µM |
| 7 | 0.890 µM |
| 8a | 15.8 µM |
| 8b | 2.1 µM |
| 8c | 3.8 µM |
| 12 | 0.694 µM |
| 13 | 0.979 µM |

2. Inhibition of cell viability and proliferation

| HCT116 | | PC3 | |
|---|---|---|---|
| Experimental N° | HCT116 GI50 D3 | Experimental N° | PC3 GI50 D3 |
| 5a | 1.402 µM | 5a | 6.15 µM |
| 5b | 1.64 µM | 5b | 6.69 µM |
| 5d | 1.01 µM | 5d | 2.79 µM |
| 6 | 0.096 µM | 6 | 0.180 µM |
| 7 | 0.363 µM | 7 | 0.466 µM |
| 8a | 0.398 µM | 8a | 0.391 µM |
| 8b | 0.273 µM | 8b | 0.457 µM |
| 8c | 0.265 µM | 8c | 0.502 µM |
| 10b | 3.36 µM | 10f | 8.4 µM |
| 10d | 3.93 µM | 12 | 0.548 µM |
| 10f | 2.1 µM | 13 | 1.97 µM |
| 10h | 1.91 µM |  |  |
| 12 | 0.412 µM |  |  |
| 13 | 0.832 µM |  |  |

The invention claimed is:
1. A compound having a formula:

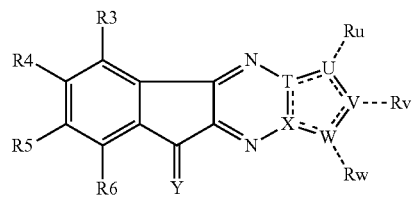

wherein:
- ⁻⁻⁻ is either a single or double bond, as appropriate;
- ------ is either none or a single bond, as appropriate;
- T, U, W, X are the same or different and are chosen from C or N;
- V is N;
- Y is N-OR1, NR'1, CR2R'2;
- R1 is H, Alkyl, Alkenyl, Alkoxyalkyl, Aryloxyalkyl, Arylalkyl, Alkoxycarbonylalkyl, Carboxyalkyl;
- R'1 is H, Alkyl, Aryl or Aralkyl;
- R2, R'2 are each the same or different and are independently selected from H, Alkyl, Aryl or Aralkyl;
- Rv is absent;
- Rw is either H or absent;
- Ru is absent or is chosen from the group consisting of H, CN, =O, Hal, Alk, OAlk, OH, NRCN, C(CN)=C(OH)(OAlk), SR, NRR', C(O)NRR', Heterocycle, Aryl, Heteroaryl, Cycloalkyl, where Alk, Aryl, Heteroaryl, Heterocycle, Cycloalkyl are optionally substituted by Hal, NRR', CN, OH, $CF_3$, Aryl, Heteroaryl, OAlk;

R3, R4, R5, R6 are each identical or different and are independently chosen from the group consisting of H, OAlk, Alk, Hal, NRR', CN, OH, OCF$_3$, CF$_3$, Aryl, Heteroaryl;

R and R' are each identical or different and are independently chosen from the group consisting of H, Alk, wherein Alk is optionally substituted by Hal, NRR', CN, OH, CF$_3$, Aryl, Heteroaryl;

or their pharmaceutically acceptable salts, or their optical isomers, racemates, diastereomers or enantiomers, or their regioisomers, geometrical isomers (E and Z) or mixtures thereof.

2. The compound according to claim 1, wherein Ru is chosen from H, Aryl, Alk, NRR', Hal, -AlkAryl, -AlkOH, -AlkOAlk, Cycloalkyl.

3. The compound according to claim 1, wherein R3, R4, R5, R6 are each identical or different and are independently chosen from the group consisting of H, Hal, Alk, OAlk, OCF$_3$.

4. The compound according to claim 1, wherein they are of formula (Ia):

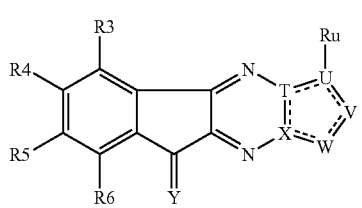

(Ia)

wherein R3, R4, R5, R6, Y, T, U, V, W, X, Ru are as defined in anyone of the preceding claims.

5. The compound according to claim 1, chosen from the group consisting of:

3-Methyl-1,2,3a,4, 10-pentaaza-cyclopenta[b]fluoren-9-one O-methyl-oxime

3-Methyl-1,2,3a,4, 10-pentaaza-cyclopenta[b]fluoren-9-one O-allyl-oxime

1-Methyl-2,3,4,10,10a-pentaaza-cyclopenta[b]fluoren-9-one O-allyl-oxime

3-Butyl-1,2,3a,4, 10-pentaaza-cyclopenta[b]fluoren-9-one O-allyl-oxime

1-Butyl-2,3,4,10,10a-pentaaza-cyclopenta[b]fluoren-9-one O-allyl-oxime 1,2,3,3a,4,10-hexaaza-cyclopenta[b]fluoren-9-one O-allyl-oxime 1,2,3,3a,4,10-hexaaza-cyclopenta[b]fluoren-9-one oxime 1,2,3,3a,4,10-Hexaaza-cyclopenta[b]fluoren-9-one O-decyl-oxime 1,2,3,3a,4,10-Hexaaza-cyclopenta[b]fluoren-9-one O-(2-methoxy-ethyl)-oxime 1,2,3,3a,4,10-Hexaaza-cyclopenta[b]fluoren-9-one O-(3-phenoxy-propyl)-oxime 1-Ethyl-2,3,4,10,10a-pentaaza-cyclopenta[b]fluoren-9-one O-methyl-oxime 3-Ethyl-1,2,3a,4,10-pentaaza-cyclopenta[b]fluoren-9-one O-methyl-oxime 1-Ethyl-2,3,4,10,10a-pentaaza-cyclopenta[b]fluoren-9-one O-ethyl-oxime 3-Ethyl-1,2,3a,4,10-pentaaza-cyclopenta[b]fluoren-9-one O-ethyl-oxime 1-Ethyl-2,3,4,10,10a-pentaaza-cyclopenta[b]fluoren-9-one O-allyl-oxime 3-Ethyl-1,2,3a,4,10-pentaaza-cyclopenta[b]fluoren-9-one O-allyl-oxime 1-Ethyl-2,3,4,10,10a-pentaaza-cyclopenta[b]fluoren-9-one O-benzyl-oxime 3-Ethyl-1,2,3a,4,10-pentaaza-cyclopenta[b]fluoren-9-one O-benzyl-oxime

[1-Ethyl-2,3,4,10,10a-pentaaza-cyclopenta[b]fluoren-9-ylidene ]-phenyl-amine (1,2,3,3a,4,10-Hexaaza-cyclopenta[b]fluoren-9-ylidene-aminooxy)-acetic acid ethyl ester (1,2,3,3a,4,10-Hexaaza-cyclopenta[b]fluoren-9-ylidene-aminooxy)-acetate lithium salt, or their pharmaceutically acceptable salts, or their optical isomers, racemates, diastereomers or enantiomers, or their regioisomers, geometrical isomers (E and Z) or mixtures thereof.

6. A process of preparation of a compound according to claim 1, comprising the step of reacting a corresponding compound of formula (I'):

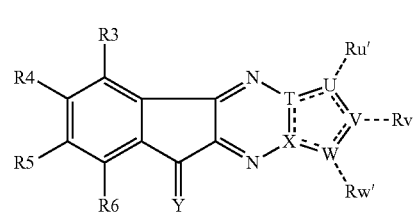

(I')

wherein R3, R4, R5, R6, T, U, V, W, X, Ru, Rv, Rw are defined as in claim 1, and wherein each of Ru', Rv', Rw' is similar to Ru, Rv, Rw or is a precursor group of corresponding Ru, Rv, Rw, and wherein the step of reacting a corresponding compound of formula (I') comprises one or more steps allowing a precursor group to be transformed into the desired Ru, Rv or Rw group, and optionally isolating the compound according to claim 1.

7. A process of preparation of a compound according to claim 1, comprising the step of reacting corresponding compounds of formula (II) and (III):

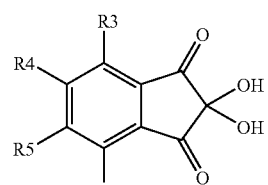

(II)

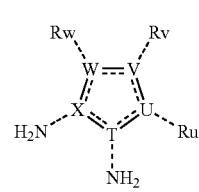

(III)

wherein R3, R4, R5, R6, T, U, V, W, X, Ru, Rv, Rw are defined as in claim 1.

8. The process according to claim 7, wherein the reaction is carried out in an organic protic solvent in the presence of an acid.

9. A pharmaceutical composition comprising a compound having a formula

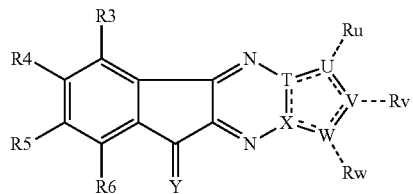

wherein R3, R4, R5, R6, T, U, V, W, X, Ru, Rv and Rw are as defined in claim 1.

10. A method for inhibiting one or more cysteine proteases, comprising administering a compound as defined in claim 1 to a patient in the need thereof, wherein the one or more cysteine proteases are selected from the group consisting of USP5, USP7, USP8, UCH-L3, and Cathepsine B.

* * * * *